(12) United States Patent
Gasper

(10) Patent No.: US 10,010,898 B2
(45) Date of Patent: Jul. 3, 2018

(54) DISPENSING SYSTEMS WITH WAVE SENSORS

(71) Applicant: S.C. Johnson & Son, Inc., Racine, WI (US)

(72) Inventor: Thomas P. Gasper, Germantown, WI (US)

(73) Assignee: S. C. Johnson & Son, Inc., Racine, WI (US)

( * ) Notice: Subject to any disclaimer, the term of this patent is extended or adjusted under 35 U.S.C. 154(b) by 937 days.

(21) Appl. No.: 13/841,229

(22) Filed: Mar. 15, 2013

(65) Prior Publication Data
US 2014/0263426 A1 Sep. 18, 2014

(51) Int. Cl.
| | | |
|---|---|---|
| B67D 1/00 | (2006.01) | |
| B05B 12/08 | (2006.01) | |
| B65D 83/22 | (2006.01) | |
| B05B 12/12 | (2006.01) | |
| B05B 1/00 | (2006.01) | |
| G01F 1/66 | (2006.01) | |
| G01N 29/14 | (2006.01) | |
| A61L 2/00 | (2006.01) | |
| A61L 9/00 | (2006.01) | |

(Continued)

(52) U.S. Cl.
CPC ............ B05B 12/081 (2013.01); A61L 2/00 (2013.01); A61L 9/00 (2013.01); B05B 1/00 (2013.01); B05B 12/085 (2013.01); B05B 12/12 (2013.01); B65D 83/22 (2013.01); G01F 1/666 (2013.01); G01N 29/14 (2013.01); B05B 11/0005 (2013.01); B05B 12/02 (2013.01); B05B 12/122 (2013.01); B65D 83/75 (2013.01); G01N 2291/02836 (2013.01)

(58) Field of Classification Search
CPC ......... B05B 12/081; A62J 1/10; A62J 1/1412; A61L 2/00; A61L 9/00; B65B 1/00; B65B 12/085; B65B 12/12; B65D 82/22; G01F 1/666; G02N 29/14
USPC ........................................ 222/52, 64–66, 68
See application file for complete search history.

(56) References Cited

U.S. PATENT DOCUMENTS

| | | |
|---|---|---|
| 3,530,888 A | 9/1970 | Cable |
| 4,410,967 A | 10/1983 | Hendricks |

(Continued)

FOREIGN PATENT DOCUMENTS

| | | |
|---|---|---|
| CN | 00320100.7 | 2/2002 |
| CN | 200730059144.5 | 7/2007 |

(Continued)

OTHER PUBLICATIONS

PCT/US2014/020116 International Search Report and Written Opinion dated Jun. 16, 2014.

(Continued)

*Primary Examiner* — Lien Ngo
(74) *Attorney, Agent, or Firm* — Quarles & Brady LLP

(57) ABSTRACT

A dispensing system includes a conduit having a volumetric capacity between an internal discharge orifice for receipt of a flow of pressurized fluid from a valving assembly and an external discharge orifice. The dispensing system further includes a volume of pressurized fluid and a sensor. The fluid has a volumetric flow rate of about 0.05 ml/ms to about 15 ml/ms when released into the conduit from the internal discharge orifice. The sensor detects a sound at the external discharge orifice.

10 Claims, 12 Drawing Sheets

(51) Int. Cl.
  *B05B 11/00* (2006.01)
  *B05B 12/02* (2006.01)
  *B65D 83/14* (2006.01)

(56) References Cited

U.S. PATENT DOCUMENTS

| | | | |
|---|---|---|---|
| 4,572,253 A | 2/1986 | Farmer et al. | |
| 4,798,232 A | 1/1989 | Stembridge et al. | |
| 4,905,897 A | 3/1990 | Rogers et al. | |
| 4,917,155 A | 4/1990 | Koblasz et al. | |
| 5,241,778 A | 9/1993 | Price | |
| 5,249,718 A | 10/1993 | Muderlak | |
| 5,314,097 A * | 5/1994 | Smrt et al. | 222/402.1 |
| 5,318,208 A * | 6/1994 | van der Wal | 222/402.13 |
| 5,449,117 A | 9/1995 | Muderlak et al. | |
| 5,473,942 A | 12/1995 | Vick et al. | |
| 5,616,845 A | 4/1997 | Hickling et al. | |
| 5,695,091 A | 12/1997 | Winings et al. | |
| 5,753,302 A | 5/1998 | Sun et al. | |
| 5,938,076 A * | 8/1999 | Ganzeboom | 222/23 |
| D430,358 S | 8/2000 | Papiernik | |
| 6,202,342 B1 | 3/2001 | Edwards | |
| 6,254,065 B1 | 7/2001 | Ehrensperger et al. | |
| 6,400,647 B1 | 6/2002 | Huntress | |
| 6,405,939 B1 | 6/2002 | Mazzenga et al. | |
| 6,438,239 B1 | 8/2002 | Kuchen | |
| D465,149 S | 11/2002 | Bennett et al. | |
| 6,574,913 B2 | 6/2003 | Takács et al. | |
| 6,617,079 B1 | 9/2003 | Pillion et al. | |
| D481,636 S | 11/2003 | Camacho | |
| 6,644,507 B2 | 11/2003 | Borut et al. | |
| 6,653,971 B1 | 11/2003 | Guice et al. | |
| D483,458 S | 12/2003 | Huang | |
| 6,712,287 B1 | 3/2004 | Pesant et al. | |
| 6,739,479 B2 | 5/2004 | Contadini et al. | |
| 6,779,905 B1 | 8/2004 | Mazursky et al. | |
| 6,795,588 B1 | 9/2004 | Nio et al. | |
| 7,020,996 B2 | 4/2006 | Beroza et al. | |
| 7,021,560 B2 | 4/2006 | Gray et al. | |
| 7,028,861 B2 | 4/2006 | Sayers et al. | |
| 7,066,029 B2 | 6/2006 | Beavis et al. | |
| 7,109,849 B2 | 9/2006 | Caine | |
| 7,146,977 B2 | 12/2006 | Beavis et al. | |
| D538,915 S | 3/2007 | Anderson et al. | |
| D541,923 S | 5/2007 | Higareda | |
| D548,317 S | 8/2007 | Newton et al. | |
| 7,271,706 B2 | 9/2007 | Lee | |
| 7,305,984 B2 | 12/2007 | Altobelli et al. | |
| 7,317,399 B2 | 1/2008 | Chyun | |
| 7,362,658 B2 | 4/2008 | Hsu | |
| 7,385,483 B2 | 6/2008 | Lee | |
| 7,411,511 B2 | 8/2008 | Kennish et al. | |
| D583,453 S | 12/2008 | Kay et al. | |
| 7,476,002 B2 | 1/2009 | Wolf et al. | |
| 7,484,860 B2 | 2/2009 | Demarest et al. | |
| D588,687 S | 3/2009 | Drucker et al. | |
| 7,501,979 B1 | 3/2009 | Guice et al. | |
| 7,541,936 B2 | 6/2009 | Wijenberg et al. | |
| D595,829 S | 7/2009 | Drucker et al. | |
| D597,192 S | 7/2009 | Drucker et al. | |
| 7,610,118 B2 | 10/2009 | Schramm et al. | |
| D608,436 S | 1/2010 | Drucker et al. | |
| 7,677,412 B2 | 3/2010 | Litterst et al. | |
| 7,712,249 B1 | 5/2010 | Modlin et al. | |
| D621,494 S | 8/2010 | Li | |
| 7,774,096 B2 | 8/2010 | Goerg et al. | |
| 7,791,490 B2 | 9/2010 | Kennish et al. | |
| 7,826,309 B2 | 11/2010 | Spanke et al. | |
| 7,830,273 B2 | 11/2010 | Twitchell | |
| D629,880 S | 12/2010 | Hisey | |
| D630,250 S | 1/2011 | Yoon | |
| D631,204 S | 1/2011 | Dubitsky et al. | |
| D632,211 S | 2/2011 | Bradley et al. | |
| D632,378 S | 2/2011 | Deflorian et al. | |
| D632,773 S | 2/2011 | Abbondanzio et al. | |
| D633,190 S | 2/2011 | Abbondanzio et al. | |
| 7,894,842 B2 | 2/2011 | Jagoe et al. | |
| 7,930,068 B2 | 4/2011 | Robert et al. | |
| 8,009,015 B2 | 8/2011 | Sayers et al. | |
| D647,187 S | 10/2011 | Chan et al. | |
| 8,070,139 B2 | 12/2011 | Nassirpour et al. | |
| 8,091,734 B2 | 1/2012 | Furner et al. | |
| D668,552 S | 10/2012 | Wisniewski | |
| D675,309 S | 1/2013 | Freeborn et al. | |
| 2002/0043568 A1 | 4/2002 | Hess et al. | |
| 2002/0144452 A1 | 10/2002 | Beroza | |
| 2003/0152603 A1 | 8/2003 | Johnson | |
| 2005/0079113 A1 | 4/2005 | Selander | |
| 2006/0076366 A1 * | 4/2006 | Furner et al. | 222/402.13 |
| 2006/0173576 A1 * | 8/2006 | Goerg et al. | 700/236 |
| 2007/0166575 A1 | 7/2007 | McLeod | |
| 2008/0067263 A1 | 3/2008 | Modlin et al. | |
| 2008/0149665 A1 | 6/2008 | Hafer et al. | |
| 2008/0156896 A1 | 7/2008 | Anderson et al. | |
| 2008/0208483 A1 | 8/2008 | Loose et al. | |
| 2008/0210772 A1 | 9/2008 | Pearce et al. | |
| 2010/0006667 A1 * | 1/2010 | Nielsen et al. | 239/74 |
| 2010/0038379 A1 | 2/2010 | Butler et al. | |
| 2010/0044458 A1 | 2/2010 | Zabari | |
| 2010/0133292 A1 * | 6/2010 | Ware et al. | 222/1 |
| 2010/0163573 A1 | 7/2010 | Wegelin et al. | |
| 2010/0186284 A1 | 7/2010 | Hyde et al. | |
| 2010/0237108 A1 | 9/2010 | Anderson et al. | |
| 2010/0270393 A1 | 10/2010 | Schumacher et al. | |
| 2010/0286803 A1 | 11/2010 | Tillotson et al. | |
| 2011/0011886 A1 | 1/2011 | Zaima et al. | |
| 2011/0222708 A1 | 9/2011 | Yu et al. | |
| 2012/0017894 A1 | 1/2012 | Cinquin | |
| 2012/0227647 A1 | 9/2012 | Gelinske et al. | |

FOREIGN PATENT DOCUMENTS

| | | |
|---|---|---|
| CN | 201030162166.6 | 5/2010 |
| CN | 201030177235.0 | 5/2010 |
| CN | 201130188926.5 | 6/2011 |
| CN | 201130238873.3 | 7/2011 |
| CN | 201130380117.4 | 10/2011 |
| CN | 201130385151.0 | 10/2011 |
| CN | 201130460329.3 | 12/2011 |
| CN | 201230337814.6 | 7/2012 |
| CN | 201030571943.2 | 10/2012 |
| EM | 000013099-0030 | 1/2003 |
| EM | 000218763-0001 | 8/2004 |
| EM | 000417779-0001 | 10/2005 |
| EM | 000792627-0004 | 9/2007 |
| EM | 000792627-0005 | 9/2007 |
| EM | 000792692-0006 | 9/2007 |
| EM | 000814355-0001 | 10/2007 |
| EM | 000814355-0002 | 10/2007 |
| EM | 000814355-0003 | 10/2007 |
| EM | 000898937-0001 | 3/2008 |
| EM | 000898937-0003 | 3/2008 |
| EM | 000898937-0004 | 3/2008 |
| EM | 000898937-0005 | 3/2008 |
| EM | 001113310-0001 | 3/2009 |
| EM | 001113310-0003 | 3/2009 |
| EM | 001113310-0005 | 3/2009 |
| EM | 001171656-0004 | 10/2009 |
| EM | 001187512-0002 | 1/2010 |
| EM | 001187512-0007 | 1/2010 |
| EM | 001710245-0001 | 5/2010 |
| EP | 2511889 A2 | 10/2012 |
| JP | 60129159 A | 7/1985 |
| WO | DM049719 | 10/1999 |
| WO | DM057578 | 9/2001 |
| WO | DM063687 | 4/2003 |
| WO | DM065068 | 11/2003 |
| WO | DM065891 | 11/2003 |
| WO | 2004010762 | 2/2004 |
| WO | 2006059059 | 8/2006 |
| WO | 2008149064 | 12/2008 |
| WO | 2009090415 | 7/2009 |
| WO | DM074361 A | 5/2010 |
| WO | 2010125141 | 11/2010 |

(56) References Cited

FOREIGN PATENT DOCUMENTS

| WO | DM076581 | 4/2011 |
|---|---|---|
| WO | 2011107752 A1 | 9/2011 |
| WO | 2011117812 | 9/2011 |
| WO | WO2011/135353 A1 | 11/2011 |
| WO | DM077856 | 3/2012 |

OTHER PUBLICATIONS

European Office Action for EP 14711401.1-1760 dated Jun. 12, 2017, 8 pages.

* cited by examiner

DISPENSING SYSTEMS WITH WAVE SENSORS

CROSS REFERENCE TO RELATED APPLICATIONS

Not applicable

REFERENCE REGARDING FEDERALLY SPONSORED RESEARCH OR DEVELOPMENT

Not applicable

SEQUENTIAL LISTING

Not applicable

BACKGROUND OF THE INVENTION

Field of the Background

The present disclosure relates to dispensing systems having wave sensing technology.

Description of the Background

Active and passive dispensers are used to deliver materials stored in containers to a surrounding environment. The materials may include volatile substances, such as fragrances, deodorants, insecticides, insect repellants, and the like. In active dispensers, such materials are diffused with the aid of fans, heaters, actuators, transducers, combinations thereof or other dynamic means for accelerating diffusion.

A common type of active dispenser receives a valve stem of an aerosol container in which the volatile material is stored. The active dispenser may trigger the valve stem to expel the material from the container, whereby the expelled material often proceeds through an additional nebulizer for dispersal as fine droplets into the atmosphere. Actuation of the active dispenser may occur in response to a manual or sensory input, or a predetermined or lapsed timed interval. For instance, an active dispenser may release a fragrant air freshener into a living room upon an activation by a user, a sensing of environmental stimuli, an occurrence of a time of day and/or a passage of a length of time. In any situation, however, the active dispenser provides diminished utility if the engaged container is depleted of the volatile material. For instance, when unrealized or forgotten by the user, the dispenser may continue to operate on an empty container, which may waste energy and batteries while providing no benefit to the user.

Attempts to indicate an end of supply have been implemented for active dispensing systems. Some dispensers count a number of emitted sprays and show when a count threshold is reached to inform the user that a refill is due. Counters, however, are unreliable since they operate independent of the actual status of the container. For instance, counters may be reset by an inadvertent user input or off-count if the user inserts a partially used or empty container.

Further, it is contemplated that there is a need for a smart dispensing system that operates based on the particular container or product received therein. Traditional dispensing systems operate with uniform dispensing methodologies regardless of the container or product used. A smart dispensing system, however, could identify a particular formulation or container and apply a best mode of operation for dispensing thereof. For instance, an inadvertent spray from an unidentified container may be avoided with a smart dispensing system capable of detecting the unauthorized container.

Presently, there is a need for an active dispenser having a sensor that is intended for sensing sound directly from the conduit of a container in order to determine a true level of material or other status of the container. There is also a need for distinguishing the sound emitted directly from the conduit from other sounds, e.g., ambient noise, actuator noise, and the like. Additionally, there is a need for a smart dispensing system that provides a reliable and optimized distribution of a volatile material. It is an object of the present disclosure to address these needs and to provide related advantages.

SUMMARY OF THE INVENTION

According to one embodiment, a dispensing system includes a conduit having a volumetric capacity between an internal discharge orifice for receipt of a flow of pressurized fluid from a valving assembly and an external discharge orifice. The dispensing system further includes a volume of pressurized fluid and a sensor. The fluid has a volumetric flow rate of about 0.05 ml/ms to about 15 ml/ms when released into the conduit from the internal discharge orifice. The sensor detects a sound at the external discharge orifice.

According to another embodiment, a dispensing system includes an external discharge orifice at an end of a conduit in fluid communication with a valving assembly. A sensor is included for detecting a sound at the external discharge orifice. The dispensing system further includes a controller having a plurality of preprogrammed operational parameters associated with a plurality of preprogrammed frequency characteristics, wherein the controller compares a frequency characteristic of the sound to the plurality of preprogrammed frequency characteristics.

According to a different embodiment, a dispensing system includes a housing acting as a waveguide and an electrically operable actuator to effect a spray from a container. A microphone is provided for detecting a sound during an actuation stage. Further, a controller is configured to determine a level of product within the container based on the sound.

According to yet a different embodiment, a method of dispensing includes the step of detecting a sound emitted from a reservoir of fluid having a conduit. Another step includes, processing the detected sound to determine at least one of (a) whether the container is full or empty; (b) whether the container needs to be replaced; (c) whether the container is authorized for use; or (d) what operational parameter to initiate.

According to a still different embodiment, a refill for a dispensing system includes a reservoir having a conduit with an internal discharge orifice and an external discharge orifice. The reservoir includes a fluid having a volumetric flow rate of about 0.05 ml/ms to about 15 ml/ms when released into the conduit from the internal discharge orifice. The conduit includes at least one of an interruption or obstruction to change a frequency of the fluid between the internal discharge orifice and the external discharge orifice, which is adapted to be detected by a sensor of a dispensing system.

Other aspects and advantages will become apparent upon consideration of the following detailed description and the attached drawings, in which like elements are assigned like reference numerals.

DETAILED DESCRIPTION OF THE DRAWINGS

Figure 1:
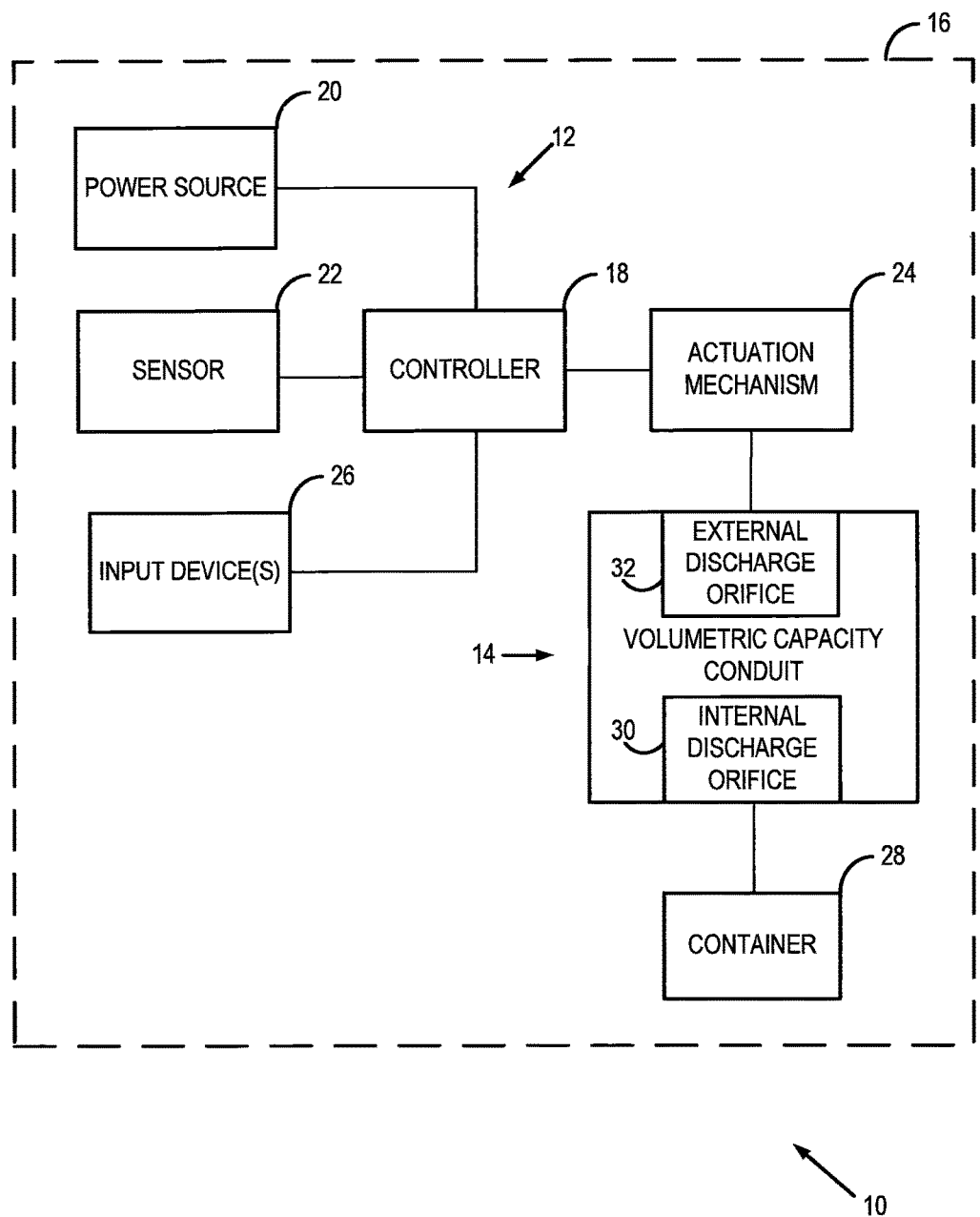
FIG. 1 is a schematic representation of a dispensing system.

FIG. 1 generally depicts a dispensing system 10 including a dispenser 12 and a conduit 14 having a volumetric capacity disposed within a housing 16. The dispenser 12 includes a controller 18 in operative communication with a power source 20, one or more sensors 22, an actuation or dispensing mechanism 24, and one or more input devices 26. The power source 22 may include one or more plugs for insertion into an electrical outlet, solar power panels, batteries, and/or combinations thereof. Further, one or more reservoirs or containers 28 containing a product may be provided wholly or partially within the housing 16.

The dispenser 12 is configured to discharge the product from one or more containers 28 upon the occurrence of a particular condition. The condition could be the manual activation of the dispenser 12 that is received through input device 26. As an example, the input device 26 may be a switch, which allows a user to turn on the dispenser 12 and/or a pushbutton, which allows the user to initiate a dispense mode of the dispensing system 10. In another embodiment, the input device 26 comprises a wireless signal transceiver for communicating with a remote device, such as a mobile phone, laptop, or other computer. The dispenser 12 may also discharge product upon automatic activation, which may occur in response to a lapsed time interval or signal from the sensor 22.

The product to be discharged is stored in the container 28 and may include a fragrance, deodorizer, insecticide, insect repellent, or other product, product formulation, or volatile fluid material. For example, the product may comprise OUST®, an air and carpet sanitizer for household, commercial, and institutional use, or GLADE®, a household deodorant, both sold by S.C. Johnson and Son, Inc., of Racine, Wis. The product may also comprise other actives, such as disinfectants, sanitizers, air and/or fabric fresheners, cleaners, odor eliminators, mold or mildew inhibitors, insect repellents, and the like, or that have aroma-therapeutic properties. The dispenser 12 is therefore adapted to dispense any number of different products. In embodiments that utilize more than one container 28, the product within the containers 28 may be the same, similar, or different. Each container 28 may be in operable communication with one or more actuation mechanisms 24, e.g., an operative connection of an output valve stem of an aerosol container with the actuation mechanism 24.

Figure 2:
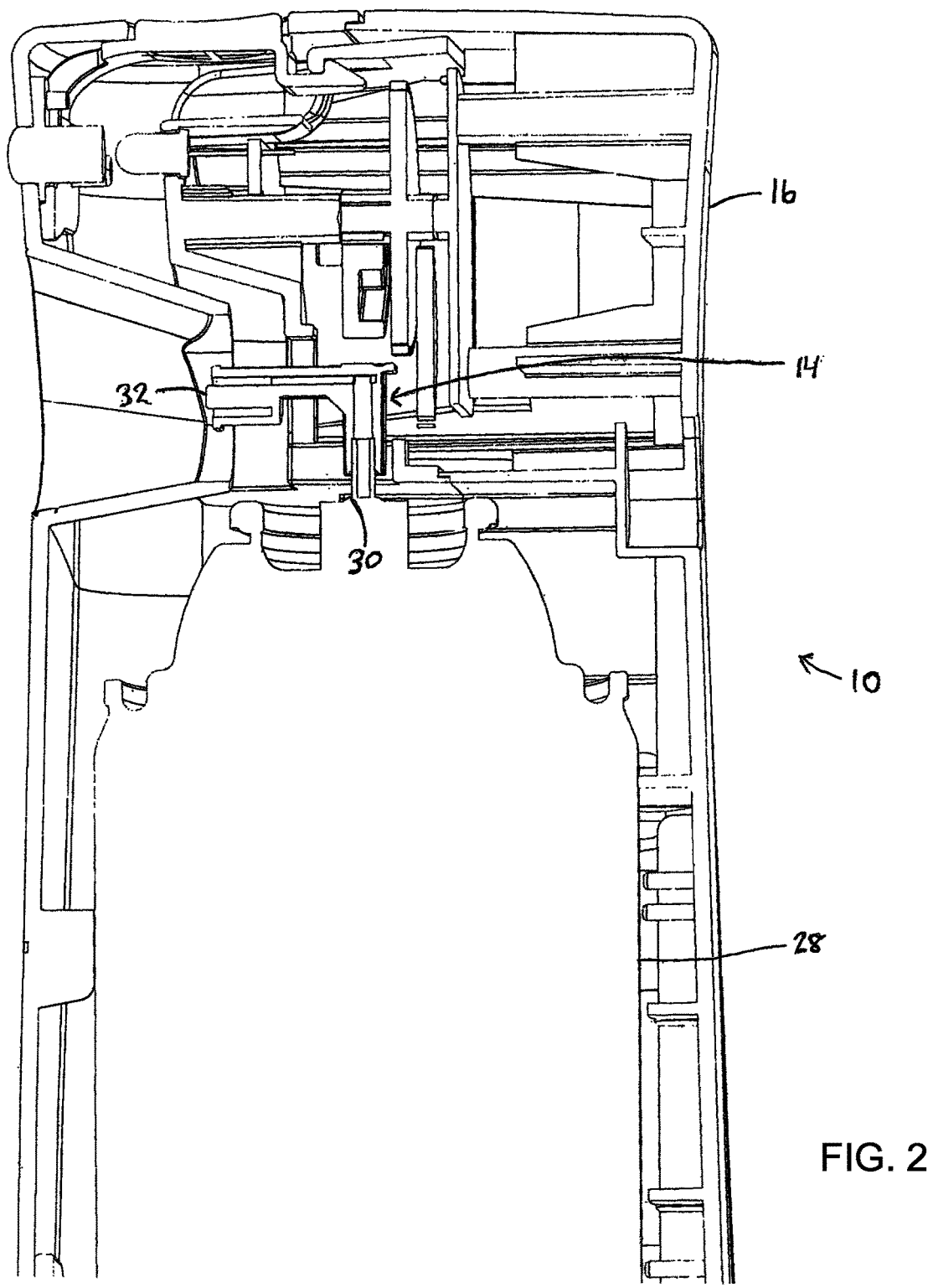
FIG. 2 is a partial cross-sectional view of a dispensing system.

Still referring to FIG. 1, the container 28 is in fluid communication with the conduit 14, which provides an internal discharge orifice 30 and an external discharge orifice 32. In particular, the internal discharge orifice 30 receives the product from the container 28 into the conduit 14 having the volumetric capacity, which provides a pathway for travel of the product to the external discharge orifice 32. Turning to FIG. 2, a partial cross-sectional view of one embodiment of a dispensing system 10 comprises a container 28 in fluid communication with a conduit 14. In the present embodiment, the internal discharge orifice 30 is provided at an aperture that is alternatively sealed and unsealed by a gasket that provides a seal between the fluid of the container 28 and the conduit 14. In connection with an aerosol or pump-type spray container 28, the internal discharge orifice 30 is best characterized as the entry point for a flow of pressurized fluid from a previously closed valving assembly and/or metered dosing chamber. The external discharge orifice 32 may comprise an outlet end where the product is ejected, and further may be disposed within the housing 16 of the dispensing system 10 or protrude outwardly therefrom. In some embodiments, the external discharge orifice 32 is further connected to a nozzle, insert, nebulizer, channel, or other spray pathway. In either case, the conduit 14 is defined between the internal discharge orifice 30 and the external discharge orifice 32. It is contemplated that the conduit 14 includes at least a valve stem of a continuous or metered dose aerosol container and at least a portion of a discharge tube of a pump-type spray container. It is also envisioned that surfaces defining an aperture may constitute the conduit in scenarios where fluid is ejected directing from a valving assembly. Further, it is noted that although the external discharge orifice 32 is positioned facing perpendicularly away from the internal discharge orifice 30, such that a ninety degree turn in the conduit 14 is required, any configuration of the pathway for the conduit 14 may be provided, e.g., straight, angled, spiraled, and the like. Indeed, the external discharge orifice 32 may best be characterized as a point of egress from a defined volume or volumetric capacity that controls the path of a fluid. In some embodiments, the external discharge orifice 32 may comprise a nozzle assembly.

Referring back to FIG. 1, the actuation mechanism 24 may be configured to spray product from the container 28. It is anticipated that the container 28 is an aerosol device, however, pump-type spray containers may also be utilized in the present embodiment. Conventional actuation mechanisms may include, but are not limited to, mechanically driven means, such as armatures, levers, linkages, cams, etc., that depress, tilt, or otherwise activate a valve stem or pump of the container 28 by direct interaction with the valve stem or pump, through indirect communication with the valve stem or pump, and/or through physical interaction with the container 28, i.e., lifting, pushing, tilting, lowering, or otherwise deflecting the container 28 to effect the depression or tilting of the valve stem or pump. It is also contemplated that solenoid actuators, bi-metallic actuators, muscle wire actuators, piezo actuators, or any other means may be utilized to effect spraying of an aerosol or pump-type container. Further, it is also contemplated that other dispensing and actuation means may be utilized, such as those used in connection with nebulizers or venturi sprayers. Still further, the dispenser 12 may include a second actuation mechanism to dispense product from a second container. The dispenser 12 may utilize the product provided within the container 28 that is pressurized or non-pressurized. For ease of discussion, one actuation mechanism 24 and one container 28 will be described unless otherwise noted.

Still referring to FIG. 1, the sensor 22 disposed within the housing 16 may detect various stimuli and communicate the sensed input to controller 18 in order to effect a response from the dispensing system 10. More specifically, the sensor 22 may detect pressure waves within the housing 16, e.g., a microphone or other sound activated sensor. In one embodiment, the sensor 22 may also detect sensory input from an external source not contained within the housing 16, such as the detection of noise from a footstep indicating that a person has entered a room. The sensor 22 might actively detect sensory input during a power on or off of the system, or cause the initiation of a pre-programmed timed sequence of dispensing, the initiation of a sequence that comprises one or more dispensing periods between one or more non-dispensing periods, the initiation of a sequence that includes a continual dispensing sequence, the initiation of an immediate dispensing of a product, the initiation of the dispensing of a product after a specified or non-specified delay, and the initiation of a dispensing sequence characterized by dispensing a product in response to one or more of a timed interval. In another embodiment, the sensor 22 and/or controller 18 may further detect actuation of the dispensing system in response to manual or automatic input after the initial detection of external sensory input, and the initiation of one or more previously noted actions in connection with a system having a single container, two containers, three containers, or any other number of additional containers.

While it is envisioned that the sensor 22 in the present embodiment is a sound sensor, it is also noted that numerous other types of sensors 22 for detecting external sensory input could be used with the presently disclosed dispensing system 10. For instance, a water sensor may be utilized to detect a level of water to effect a spray. A pressure sensor may detect the weight of a foreign object on the dispensing system 10 to prohibit or allow for spraying. In yet another embodiment, a humidity sensor may activate the dispenser 12 when the air is too dry or too moist. Still further, a temperature sensor that registers changes in ambient temperature may be provided to activate the dispenser 12. An odor sensor could detect certain molecules in areas such as a bathroom or kitchen and activate the dispenser 12 immediately or at a particular time following such detection. Any of the above sensors could be used alone or in connection with a motion sensor, e.g., a passive infrared or pyroelectric motion sensor, an infrared reflective motion sensor, an ultrasonic motion sensor, or a radar or microwave radio motion sensor, or more particularly a photo transistor that detects high and low peaks of light transitions. It is noted that while only one sensor 10 is discussed, any combination of such sensors could be used in the dispensing system 10. For example, a sound sensor could be used to detect a sound, frequency, change in pressure, etc., from an external direction and another sensor, e.g., a light sensor, could be used to detect motion to cause the dispenser 12 to initiate a pre-programmed response, such as a fluid spray, as noted above. In some embodiments, the light sensor may incorporate a passive infra-red sensor, such as a Panasonic PIR MP motion sensor AMN 1 (as manufactured by Panasonic), a laser sensor, or a flickering sensor that provides a wide field of view. In a particular embodiment, the light sensor is a phototransistor that detects the intensity of light and outputs electrical signals to the controller 18, which filters and processes the signals. If the controller 18 determines that a threshold light condition has been reached, i.e., a predetermined level of change in light intensity has been received by the phototransistor over a short interval, the controller 18 then determines whether to activate a spray. In some embodiments, the controller 18 determines whether to activate a spray based on both input from the sound sensor and the phototransistor. Further, it is noted that the present listing of potential sensors 22 is not exhaustive but is merely illustrative of the different types of sensors 22 that can be used with the dispenser 12 described herein.

The housing 16 containing some or all of the components of the dispenser 12 may be constructed in an aesthetically pleasing manner such that the dispensing system 10 may be left in "plain view" and positioned prominently within a room or space as desired by a user. The housing 16 may also be designed for placement in more discreet locations. In some cases, the housing 16 may be disguised in the likeness of other functional objects or decorative pieces, e.g. a rock, ornament, figurine, lamp, etc., such that the dispensing system 10 and its related functionalities are more subtle or undetectable in appearance. The housing 16 may be constructed from any suitable material, such as plastic, metal, glass, or combinations thereof. Additionally, the materials may include combinations of manufactured, natural, and recycled or reclaimed materials. The housing 16 may be any shape or any color known to those skilled in the art. In some cases, the materials selected to construct the housing 16 are configured to emulate naturally occurring substances, such as wood, stone, paper, or rock, or combinations thereof. In another aspect, the housing 16 may be shaped or colored to match that of the container 28 to be operated with the dispenser 12, or configured to receive a whole or a portion of the container 28.

Figure 3:
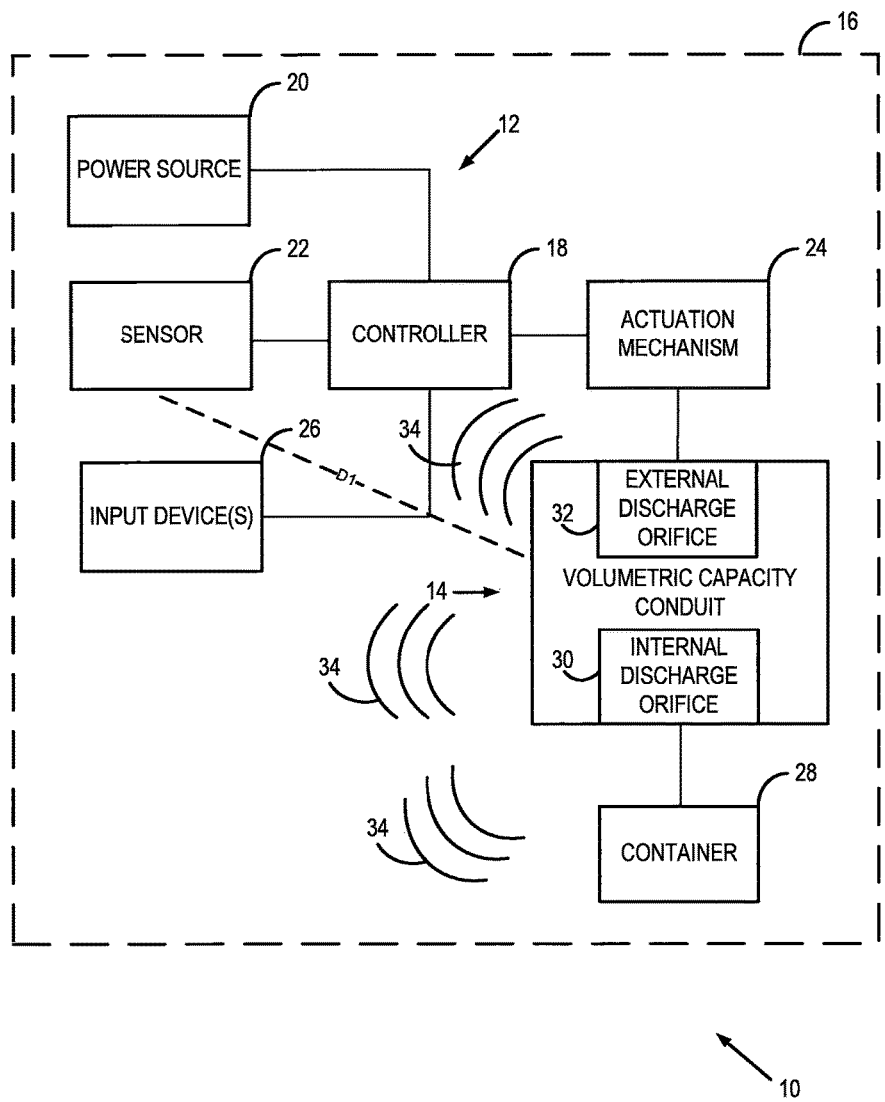
FIG. 3 is a schematic representation of a dispensing system during activation.

Turning now to FIG. 3, the dispensing system 10 of FIG. 1 is shown in an activated state when a spray is emitted. The pressure waves or acoustic waves 34 are generated at the conduit 14 when the container 28 and/or conduit 14 are activated during a spray sequence, e.g., during an egress of fluid from the container 28, through the conduit 14 and out of the external discharge orifice 32. The sensor 22 may be positioned at a linear distance D1 away from the external discharge orifice 32 of the conduit 14, whereby the maximum distance D1 shall be limited by the physical confinements of the housing 16, which encases all of the components, including some or all of the container 28. It is contemplated that the distance D1 ranges between 0 cm to about 30 cm. In one particular embodiment, the distance D1 is zero or substantially zero, whereupon the sensor 22 is affixed and/or adjacent to the conduit 14. In a different embodiment, the distance D1 is about 5 cm to about 12 cm and preferably no more than about 8 cm. In a different aspect, the structure of the housing 16 provides waveguide properties that benefit the operation of the sensor 22, such as by containing and guiding some or all of the acoustic waves 34 as described in further detail below.

In one embodiment, the sensor 22 is a microphone or other sound measuring device, e.g., a speaker used to pick up sound signals or configured to detect the acoustic waves 34 emitted from the conduit 14. The sound sensor 22 may be a microelectromechanical system ("MEMS") microphone, electret microphone, fiber optic microphone, or any other type of microphone known in the art that can be placed within the housing 16. Further, various sound sensors 22 provide different sensory field or pickup patterns, including omnidirectional, bidirectional, cardioid, hypercardioid, shotgun, or any other pattern known in the art. In one embodiment, the sensor 22 is an omnidirectional MEMs microphone mounted within the housing 16 on a circuit board of the controller 18. In another embodiment where specific sensing angles are desired, e.g., a narrower sensing beam optimized for the detection of acoustic waves 34 emitted by the conduit 14, a unidirectional or other directional sensor 22 is preferred. Directional sensors 22 may further limit background noise, such as activity in the room in which the dispensing system 10 is placed. Furthermore, a directional response may be effectively created with a plurality of omnidirectional microphones that are configured into a beamforming array within the housing 16. It is contemplated further that the background noise may be effectively eliminated by use of two microphones. For instance, a first microphone may be placed closer to the conduit 14 or sound source and a second omnidirectional MEMs microphone may be placed farther away from the conduit 14, such as approximately 2 cm farther away. Since farfield noise, i.e., background noise, is detected at substantially the same levels by both microphones, and nearfield sound, i.e., sound emitted at the conduit 14 during actuation, is detected at greater level differences between the two microphones due to their different placements from the sound source, a differential amplifier may be applied to amplify the signal difference between the two microphones and thereby create a differential signal that has effectively eliminated background noise. Such differential signals having isolated actuation sounds may be particularly applicable for various applications described in the succeeding paragraphs. It is noted that other methods for improving signal-to-noise ratio of the sensors 22 are known in the art, and that selection of the type of microphone or other sensor 22 may be based at least in part on cost, weight, size, manufacturing ease, microphone sensitivity and other specifications.

Figure 6:
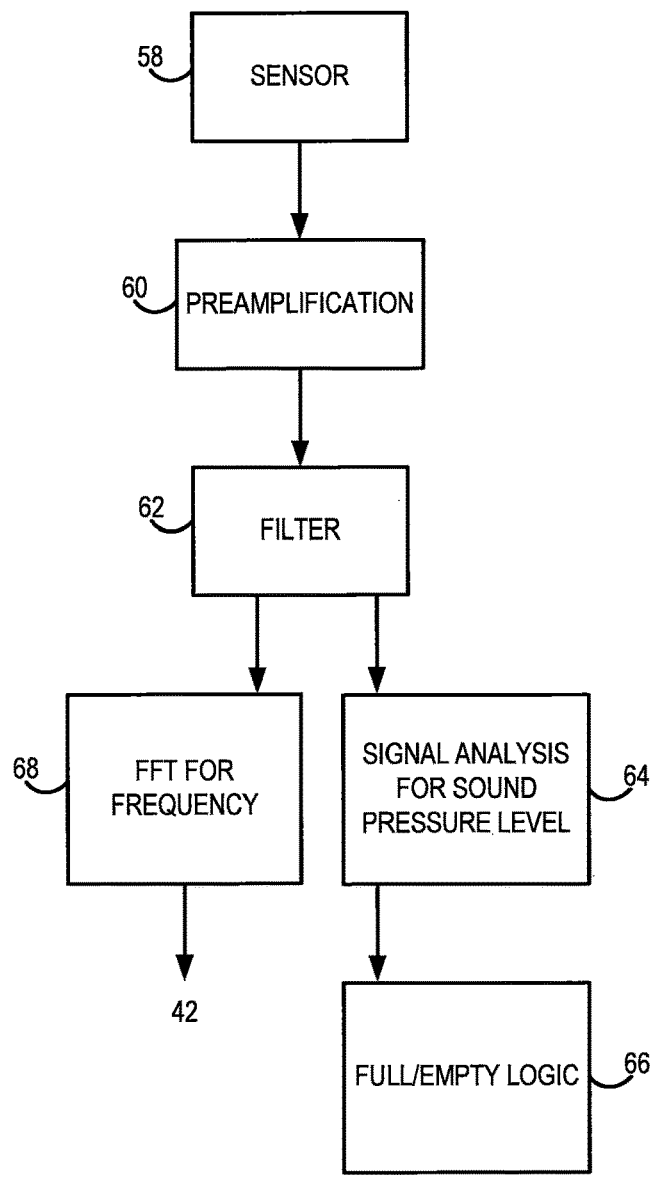
FIG. 6 is a flow chart of a method for implementation of a wave sensor in a dispensing system.

Upon detection of the acoustic waves 34, the sensor 22 converts the waves 34 into electrical signals for further processing, as described in further detail at FIG. 6. The processing may include analysis of wave properties, such as frequency, wavelength, amplitude, sound pressure, sound intensity, and various other properties or measurements known in the art. Such characteristics of the acoustic waves 34 are functions of the internal pressure of the container 28 and the mechanical design of all or a portion of the surfaces defining the volumetric capacity of the conduit 14, e.g., a mechanical design of the output valve of an aerosol container. In a non-limiting example, the properties of the acoustic waves 34 generated at the conduit 14 may be utilized to indicate properties of the container 28, including whether the container 28 is full, partially full or empty; differentiate fluid formulations of the material within the container 28; differentiate the container 28 from other containers; and the like, as described in further detail below.

For instance, the conduit 14 is a restricted passageway from which a volume of pressurized fluid or product stored inside the container 28 is released. As a spray is induced, the product is propelled through the internal discharge orifice 30 from a valving assembly or metered dose chamber with a force provided either by a high internal pressure profile of an aerosol container 28 or an upward draw of the product by a suction created with a pump-sprayer. The product continues as a flow of pressurized fluid through the volumetric capacity of the conduit 14 and is ejected from the external discharge orifice 32 with rapid speed toward a lower ambient pressure of the environment. The flow, typically turbulent and highly energetic, generates sound by vibrating the ambient air particles and creating shear forces across surface areas in its flow pathway, i.e., the conduit 14, the internal discharge orifice 30 and/or the external discharge orifice 32. The sound travels as compression waves or acoustic waves 34 that are detected by the sensor 22. Specifically, the sensor 22 may detect sound that is emitted at the external discharge orifice 32, and/or sound emitted from a surface of the conduit 14 that may be designed to generate more turbulent flow and effect the sound profile (see FIGS. 4A-D). Particularly with a full aerosol container 28, the discharge produces acoustic waves 34 at higher vibrational amplitudes due to the higher velocity of materials, or volumetric flow rate, being forced out of the pressurized container 28. As such, the acoustic waves 34 can indicate a high volumetric flow rate of the product through the conduit 14. In particular, the acoustic waves 34 have high amplitudes that are detected by the sensor 22 and correspond to high sound pressure levels. The controller 18 may further determine that given the high sound pressure level, the container 28 is full or not yet depleted. On the other hand, a lower sound pressure level detected during activation may correspond to a low volumetric flow rate and indicate that the container 28 is less full or empty. Further, it is noted that while the sensor 22 is discussed as detecting sound from particular portions of the dispensing system 10, such as the conduit 14 and the external discharge orifice 32, it is intended that the sensor 22 is capable of detecting sound from all portions of the dispensing system 10. For instance, the sensor 22 can detect sound emitting from any sound source, such as through the conduit 14 walls, through the container 28 walls, from a spray head in fluid communication with a valving assembly, and so forth. Even further, it is noted that the sensor 22 can be placed anywhere internal to the housing 16, on an internal or external surface of the housing 16, on the container 28 itself, and so forth.

In one particular embodiment, it is anticipated that the volumetric flow rate through a conduit 14 of a full container 28 holding an aerosolized product is about 0.05 ml/ms to about 15 ml/ms and that the same container in an empty or low fill state has a volumetric flow rate of about 1 ml/ms to about 0 ml/ms. In the present embodiment, the container 28 has an internal pressure of 65 psig at 23 degrees Celsius in a full state and about 0 psig at 23 degrees Celsius in an empty or low fill state. Further, the present embodiment includes a conduit having a volume of about 14 $mm^3$ and the container has a volume of about 310 $cm^3$ of product. In one particular embodiment, a container has a volume of about 15 $cm^3$, a conduit volume of about 12 $mm^3$, an internal pressure of about 65 psig at 23 degrees Celsius and a volumetric flow rate of about 1 ml/ms in a full condition and a volume of about 0 $mm^3$, an internal pressure of about 0 psig at 23 degrees Celsius and a volumetric flow rate of about 0 ml/ms in an empty or low fill state. In a different embodiment, a container has a volume of about 225 $cm^3$, a conduit volume of about 12 $mm^3$, an internal pressure of about 65 psig at 23 degrees Celsius and a volumetric flow rate of about 1 ml/ms in a full condition and a volume of about 9 $mm^3$, an internal pressure of about 0 psig at 23 degrees Celsius and a volumetric flow rate of about 0 ml/ls in an empty or low fill state. It is also contemplated that other containers with varying fluids and mechanical conduit properties may have previously noted attributes that are larger or smaller and that may fall above, below, or within any of the previously noted ranges.

The determination of a full or empty container 28 may be based on a threshold sound pressure level that is known for full or empty containers 28 and preprogrammed into the controller 18 for implementation during a full or empty control logic. In particular, the threshold sound pressure level may be set at a minimum value on a range of low sound pressure levels that are expected for low or near empty containers 26. It is contemplated that such minimum values may range from about 20 dB to about 30 dB as measured from a sensor 22 at close proximity to the conduit 14, such as within the housing 16. In one embodiment, determining the full or empty status of a container 28 comprises detecting the sound that corresponds to the level of volumetric flow rate through the conduit 14 by the sensor 22. If the sensor 22 detects a low volumetric flow rate, i.e., detects a sound pressure level that is substantially at and/or below the threshold sound level, the container 28 may be indicated as low or empty at a second stage, depending on where the threshold level is set. For instance, the threshold level may be set at a point that distinguishes between any outflow from the container 28 and zero outflow, or at a near empty point in which outflow from the container 28 is low but not completely empty. Such threshold levels may be set for indicating that the container 28 has anywhere from $\frac{1}{3}^{rd}$ to $\frac{1}{10}^{th}$ of the product remaining. On the other hand, if the sensor 22 detects a high volumetric flow rate, i.e., detects a sound pressure level that is greater than the threshold sound level that corresponds to low flow rates, the container 28 may be indicated as having a positive level of product at such first stage, which represents a full or operable status. It can be contemplated that a ratio of the threshold level to the detected level of sound during an actuation state is less than one at a first stage and substantially unity at a second stage. Similarly, it is contemplated that a ratio of the level of volumetric flow rate during an actuation state to a threshold level of volumetric flow rate is less than one at a first status and substantially unity at a second status. Further, it is contemplated that a user perceivable cue is produced by the dispensing system 10 to provide indication of the first and/or the second stage or status of the container 28. Such cues may include illumination of a light or emission of a beeping sound in various distinguishable patterns.

It is noted that the drop in internal pressure of the container 28 may not occur until the container 28 is mostly depleted. For a liquid product and liquid propellant mixture, the liquid propellant maintains the internal pressure during multiple uses by shifting enough of the liquid propellant into a gaseous phase to maintain the internal pressure as space is created when product exits. Such liquid propellants may include mixtures of butane and propane, otherwise known as liquid petroleum gas or LPG. In this mixture, the pressure within the container 28 remains effectively constant and spray performance is maintained through most of the life of the aerosol. For a liquid product and compressed gas propellant mixture, the volume of gas within the container 28 is constant such that more space is created as product exits and the pressure drop is more evident over the life of the aerosol. Compressed gas propellants may include nitrogen, nitrous oxide, air and carbon dioxide. Although the pressure reduces as the liquid product runs down, modifications are contemplated for improving the spray performance such as product formulations that shift from liquid to gas phase as the pressure permits, or other vapor-pressure curve designs. In view of the foregoing, the threshold level for a container 28 having a substantially constant pressure throughout its life is most likely to be set at a point distinguishing full and empty status. On the other hand, the threshold level for a container 28 having a greater range in pressures, i.e. decreasing pressure over a lifetime, might have a larger range of threshold values to discern various states of the container 28, i.e. full, empty, ¼ full, ⅓ full, and the like. In one embodiment, multiple threshold values may be set and queried against by the controller 18 to determine and indicate multiple states of the container 28, such as half full, third full, quarter full, etc.

Figures 4A, 4B:
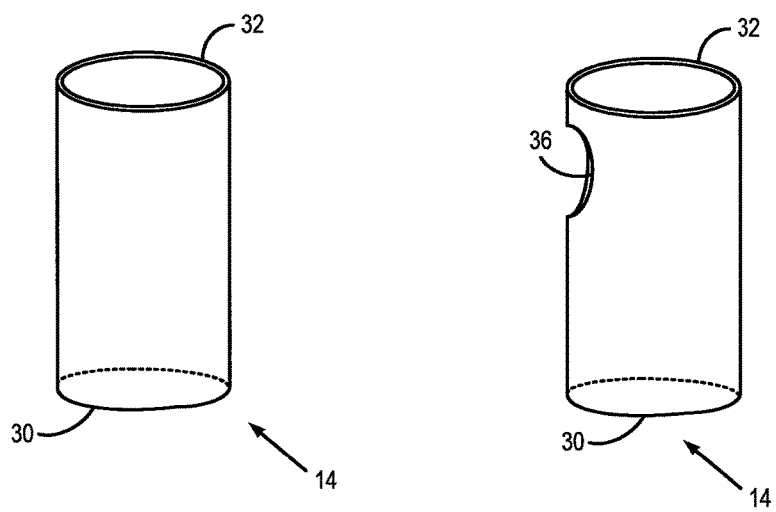
FIGS. 4A-D are several views of various conduit configurations.
Figures 4C, 4D:
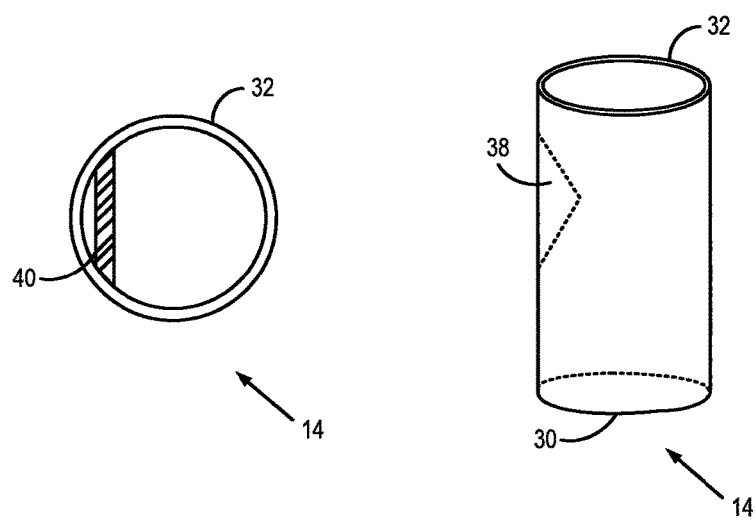

In another aspect, it is contemplated that the mechanical structure of the surface(s) defining the volumetric capacity of the conduit 14, the internal discharge orifice 30, and/or the external discharge orifice 32, can alter the sound profile detected by the sensor 22. In particular, any obstructions or interruptions in the flow pathway of the volumetric flow during emission may cause pressure differentials and create turbulence, which may alter the frequencies of the pressure waves that are emitted such that a unique sound is generated. In one embodiment, it is contemplated that the frequency characteristics of the acoustic waves 34 may be analyzed in order to identify or simply distinguish different types of containers 26. Turning to FIGS. 4A-D, various nonexclusive examples of physical modifications to the conduit 14 that may be implemented to create unique sound profiles are shown. A generally cylindrical conduit 14 is depicted in FIG. 4A and may include a groove 36 (see FIG. 4B) to create a whistle-like sound, to create sound in conjunction with a wall of a cap covering the groove, or to serve as an additional external discharge orifice 32. In another embodiment, the conduit 14 may include a wedge 38 (see FIG. 4D) at any position between an external discharge orifice 32 and an internal discharge orifice 30. In another example, a protrusion 40 extends across a portion of the external discharge orifice 32 or radially within the conduit 14 that may alter the sound (see FIG. 4C). Similarly, a flow restriction device positioned proximal to, on, or extending within the external discharge orifice 32 may create a unique sound profile for a generally cylindrical conduit 14 (see FIG. 4A). The unique sound may comprise an audible sound, such as a whistle tone or any other tone that the sensor 22 may be configured to detect, e.g., a notch filter can be added to the sensor 22 and amplification circuitry on the controller 18 to listen for specific frequencies or combinations thereof and filter out unwanted frequencies. Inaudible levels at sub or ultra-hearing frequencies may also be utilized such that the user is not disturbed.

Further, the dispensing system 10 may initiate certain operational modes in response to the frequency characteristics that are detected. For instance, detected frequency characteristics that are not matched with certain frequency characteristics, which may be preprogrammed into the controller 18 and attainable by physical modification to the conduit 14, may trigger an operational mode that prevents activation of the dispenser 12 and/or provides a cue to the user that the container 28 should be replaced, e.g., a light may be illuminated or an audible noise may be emitted to indicate that the container 28 is not an appropriate container 28. Such "classifying" detection mechanisms may be implemented to prevent unauthorized use, e.g., an unrecognized container 28 refill connected to or otherwise in association with the dispensing system 10. In a different embodiment, the controller 18 may be preprogrammed to recognize particular frequency profiles generated from a plurality of conduit 14 configurations, which may be uniquely associated with particular containers 28. When a frequency profile is recognized or allowed, the controller 18 may modify an operational mode by implementing a preprogrammed unique threshold value, activating a spray according to unique time intervals or other operational parameters, and the like, which may be associated with a particular container 28 and/or the same for all containers.

In a different embodiment, the frequencies detected can be utilized to discriminate between different product formulations, e.g., an ejected stream of gas and/or liquid may be more or less dense, or viscous, depending on its formulation and thereby generate different frequencies and/or sound pressure levels. For instance, a sound pressure level or frequency characteristic may distinguish between particulates that are smaller or larger in size. In a particular embodiment, a frequency characteristic of the fluid formulation and the conduit 14 shape may be combined in a single profile such that any deviations due to the fluid formulation or a differently shaped conduit would trigger a classifying response. In another embodiment, the frequency characteristics of the fluid formulation and the conduit shape are discernible, i.e., have different frequency profiles, such that any formula may be utilized within an allowed container 28, or any container 28 may be utilized given an allowed formula of material disposed within it. The dispensing system 10 may be configured to adjust to more optimal operational parameters for specific formulas, and/or apply any of the above identified operational modes. Furthermore, it is contemplated that many fluid properties may effect the detection of the sensor 22 and various types of sensors described above. The classifying mechanism recognizing a frequency characteristic, or even a sound pressure level, may be based on one or any combinations of properties such as density, dynamic viscosity, kinematic viscosity, conductivity, diffusivity, specific heat, and the like.

Figure 5:
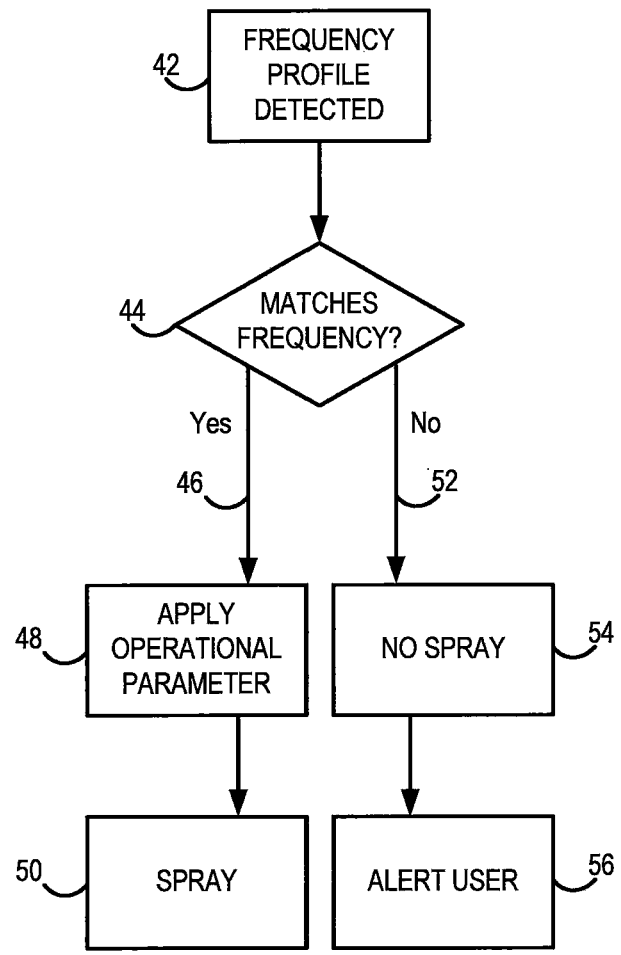
FIG. 5 is a flow chart of a method for implementation of a classifying mechanism.

Turning to FIG. 5, a flow chart is shown for a discrete portion of a classifying mechanism operational methodology. First, a frequency profile is detected by the sensor 22 at 42 upon spraying a fluid from the container 28. The frequency profile may reflect one or both of the product formulation and the surface(s) defining the volumetric capacity of the conduit 14. The frequency profile is queried against one or a plurality of preprogrammed frequency ranges at 44 to determine if the profile falls within a range or otherwise matches with a preprogrammed frequency profile. If the frequency profile is within the range or is otherwise determined as allowable at 46, then an operational parameter associated with the matched preprogrammed frequency may be applied at 48, such as checking for a preprogrammed unique threshold value associated with the frequency profile that may be applied to determine if the container 28 is full or empty or modifying a time sequence of a spray. Additionally, the controller 18 may initiate an operational state, register the allowability of a subsequent spray sequence, provide for the illumination of one or more lights or other user perceivable cue, etc. Subsequently, a spray may be activated at 50 and the process repeated during a later actuation stage. If the frequency profile is determined to not match a range at 52 or is otherwise determined as not allowable, then no spray is emitted from the dispensing system 10 at 54 and the user is alerted at 56 of the rejected container 28. Still in yet a different embodiment, the sensor 22 may be configured or hardwired to detect only certain frequency characteristics and to not detect or even register others. It is contemplated that only containers 28 producing a recognizable frequency characteristic during an activation are allowed to continue to be sprayed. For instance, the spray may be interrupted for foreign containers 28 such that little to no spray is emitted, and/or no subsequent sprays are allowed after it is determined that a foreign container 28 is being used. It is worth noting that the frequency profile, frequency distribution, and frequency characteristics are all relevant, taken together and/or individually, to the methods described herein and may be used interchangeably, and further that use of any one term is not to be construed as limiting.

In a further embodiment, the controller 18 is configured to process a third sound detected by the sensor 22 corresponding to background noise or background noise cues, such as clapping, footsteps, pre-programmed variations in sound volume of background noises, and the like. For instance, certain frequencies related to background noises may be preprogrammed to the controller 18 and queried against upon detection by the sensor 22. It is contemplated that such processing may be utilized to register sounds during an inactive period or state in order to effect a spray or other operational procedure, or applied during a spray actuation from the container 28 to extend the spray sequence or effect some other preprogrammed operation.

It is contemplated that the classifying operational methodology described above may be utilized in combination with refill containers 28, and specifically with identifying a refill container 28 according to a unique sound that enables use of the container 28 in the dispensing system 10. Such refill containers 28 may have selectively designed valve stem or conduit 14 features that are adapted to produce certain sound signatures which are recognizable by the sensor 22 and/or controller 18. For instance, the sensor 22 may be manufactured to detect only sounds within a particular frequency band, or the controller 18 is programmed to register only particular frequencies or level ranges, or combinations thereof. Likewise, the refill container 28 may be designed to generate only sounds within those identifiable frequency or level ranges, or combinations thereof.

It is also contemplated that such a refill container 28 may have a variety of physical dimensions that are modifiable to achieve the classifying purposes, such as the container size and the structural attributes of the valving assembly and the conduit 14. In one embodiment, the refill container 28 is an aerosol container that has a valve stem that is about 1.5 mm in diameter and about 8 mm long. The refill container 28 may include an outer diameter of about 22 mm and an external height of about 60 mm. Such a container 28 may also include an internal metered valve having a dose volume of about 51 ul. In a different embodiment, the refill container 28 may comprise an outer diameter of about 22 mm and an external height of about 95 mm. Such a container 28 may also be provided with a metered valve having a dose volume of about 91 ul. In yet another embodiment, the refill container 28 may comprise an outer diameter of about 65 mm and an external height of about 120 mm with no metered valve. Turning to FIGS. 4A-D, it may be further seen that conventional conduits 14 of containers 28 may also be modified. Modifications to the conduit 14 allow for the generation of a particular sound signature when product is emitted from the container 28. Furthermore, it is contemplated that the recognizable sound signature is generated based on a combination of the refill container 28 design and features of the dispensing system 10, such as a nozzle design, frequency or sound characteristic of a dispensing motor, etc. These modifications and ranges are merely exemplary and it is anticipated that any size container or conduit may be used, whether in a metered or non-metered aerosol container or a conventional or pre-compression pump-type spray container.

It is further contemplated that fluid properties of the product within the refill container 28 also contribute to the sound signature that is recognizable by the sensor 22 and/or controller 18 of the dispensing system 10. The unique sound contributed by any fluid properties may be taken alone or in combination with the above mentioned physical designs of the refill container 28. In particular, it is contemplated that fluid properties such as density, dynamic viscosity, kinematic viscosity, conductivity, diffusivity, specific heat, etc., contribute to the sound generated by the flow of product through any portion of the container 28, valving assembly or pump tube, and/or modified or unmodified conduit 14. For instance, the fluid formulation of a particular product in the refill container 28 may be adapted to create certain sound profiles by careful selection of certain volatile and nonvolatile materials comprising the fluid.

Merely by way of example, one product formula with an NIP-62 propellant, as known in the art, can have a density of about 0.63 g/cm$^{-3}$ at 70 degrees Fahrenheit and about 0.60 g/cm$^{-3}$ at 130 degrees Fahrenheit. In a different embodiment, a product formulation with an A-91 propellant, as known in the art, can have a density of about 0.75 g/cm$^{-3}$ at 70 degrees Fahrenheit and about 0.72 g/cm$^{-3}$ at 130 degrees Fahrenheit, whereas with a different product formulation and the same A-91 propellant, a product mixture may have a density of about 0.74 g/cm$^{-3}$ at 70 degrees Fahrenheit and about 0.71 g/cm$^{-3}$ at 130 degrees Fahrenheit. It is also anticipated that the density of the product may range from about 0.001 g/cm$^{-3}$ degrees Fahrenheit to about 0.49 g/cm$^{-3}$ at −40 degrees Fahrenheit. Further, it is contemplated that the contents of an LPG aerosol may have a density of about 0.5 g/cc to about 1.5 g/cc, a dynamic viscosity of about 0.3 centipoise to about 500 centipoise, and a pressure of about 17 psi to about 100 psi at 70 degrees Fahrenheit. The contents of compressed gas aerosols ("CGA") generally have a density of about 0.7 g/cc to about 1.5 g/cc, a dynamic viscosity of about 0.5 centipoise to about 500 centipoise, and an initial pressure from about 80 psi to about 180 psi at 70 degrees Fahrenheit. However, it is considered that any of the pressurized or non-pressurized fluids described herein may have a dynamic viscosity of about 0.1 centipoise to about 10,000 centipoise and a kinematic viscosity of between about 0.1 cSt and about 1,000 cSt. Furthermore, emulsion properties can be considered, with LPG aerosol contents having either an oil-out or water-out emission with internal particles sized at approximately about 0.3 microns to about 10 microns, while CGA aerosol formulas are water-out emissions with internal particle sizes from about 0.2 microns to about 10 microns. However, it is considered that any of the pressurized or non-pressurized fluids described herein may have a particle size ranging from about 0.1 microns to about 1,000 microns. As a further consideration, the pressure within a CGA type container after the contents are expelled is approximately 30 psi or more, and may be 15 psi or more. The LPG type container has a pressure that remains fairly constant over the lifetime, as stated previously, although a 50 percent reduction in pressure may occur whereby the end of life pressures may range between about 8 psi to about 100 psi, i.e., the LPG type container may be considered to be low or empty.

It is contemplated that the above fluid properties of various product formulations, along with the selected LPG or CGA container type, can contribute to different frequency distributions and sound levels of the sound generated by the product flow, and that some of the unique frequency distributions may vary in the human hearing range, which is approximately 20 Hz to 20,000 Hz, and/or vary in sub human hearing frequencies below 20 Hz, and/or vary in high frequencies above 20 kHz. In one embodiment, fluid properties of the product formulation and propellant discharged from an aerosol canister have the most noticeable effect on measured sound pressure levels at frequencies between 10 kHz to 30 khz.

A test was conducted to measure and compare the sound pressure level generated by the efflux of material from an empty container and from a full container. The measurements were taken by a Knowles MEMs microphone, e.g., a Knowles SPU0410HR5H-PB made by Dover Corp. of Downers Grove, Ill., which was placed within an inner housing of a dispensing system and at a distance of 8 cm from the conduit of an aerosol container. The microphone was connected to an AS3430 evalboard made by Austriamicrosystems of Unterpremstaetten, Austria, that provided microphone preamplification properties with a 30 dB gain. A reference microphone, GRAS Type 40AF made by G.R.A.S. Sound & Vibration of Holte, Denmark, was placed at a closer distance of 4 cm from the conduit. Raw signals were collected by the microphones and signal analysis was performed, without filtering, on a timeframe during the pull down phase of the motor that pressed down a conduit, which included a valve stem of an aerosol container. Specifically, the motor was a Model AR500V-18280-32 made by Action Motor Manufactory Limited of Hong Kong, China. It is noted that a variety of motors are available for use, such as the Techni Micro RT-500PA-18280-32 made by Techni Micro Motor Factor of Dongguan, China, and other micro and/or brushless motor devices. The dispenser, and more particularly the mechanism for actuating the conduit, was an actuator device described in Carpenter et al. U.S. patent application Ser. No. 11/725,402.

TABLE 1

Sound Pressure Level Measurements (dB)

| Container Status | Max Peak Level Measured | Max RMS Level Measured |
|---|---|---|
| Full | −6 | −10.5 |
| Empty | −20 | −30 |

Table 1 shows that the "difference" in the sound pressure level readings between a full and an empty container is at peak 14 dB and root mean square ("RMS") 19.5 dB. A clear difference in the sound pressure level is detected between the full and the empty containers. The additional reference microphone outside of the housing near the spray nozzle confirmed the results showing similar differences between the full and empty containers.

Further, it is noted that there was a significant difference in motor noise when actuating a full or empty container. This difference, however, was found mostly in the frequency characteristics of the noise rather than the sound pressure levels, i.e., a unique sound rather than a level change during actuation. It is contemplated that such differing characteristics of motor noise and sound pressure level between full and empty containers may have useful implications in distinguishing sources of sound during a detection state of the microphone. In particular, it is contemplated that noise from the mechanical structure of the dispenser 12, such as motor noise during activation, can be filtered out of the overall sound pressure level detected based on certain frequency characteristics, e.g., filtering out a frequency band associated with the motor, detecting or analyzing only data within a non-motor frequency range, and the like, so as not to confound the required sound data. Alternatively, the noise from the mechanical structure of the dispenser 12, such as motor noise during activation, may be compared to preprogrammed frequency threshold levels to use the change in frequency of the motor to determine a fill state of the container 28.

A frequency domain analysis was further performed on the signals obtained in the test above. The analysis showed noticeable sound pressure level changes occurring in the high frequency ranges between 10 kHz and 30 kHz as measured by the MEMs microphone that best detects at frequencies above 5 kHz. Therefore, it is contemplated that a range of frequencies, such as frequencies below 10 kHz, can be cut off by a second or higher order high pass filter. Implementation of such filtering can improve immunity against any background noise, such as noise from other sources in a room and sound emitted by the dispenser 12 as described above in regard to a motor. Analyzing only particular frequency ranges may also lower computational burdens. Furthermore, it is contemplated that for such a high pass filtered signal, detection of the RMS level can be accomplished in an analog domain. Even further, it is contemplated that changes in the frequency distribution of the captured sound from the container may be utilized to indicate a full or empty status of the container. For instance, certain frequency characteristics may be effected by unique sounds that correspond to different flow rates. Such characteristics may be further effected by flow across mechanical structures of the flow pathway. In one embodiment, a higher frequency may correspond to a high flow rate while a lower frequency corresponds to a low or minimal flow rate. The sensor 22 may detect such frequency characteristics and the controller 18 may be programmed to identify a status of the container based on frequency characteristics.

Turning now to FIG. 6, a flowchart shows a particular method of the present embodiment. A sound profile generated during emission of a spray is detected at the sensor 22 at 58. It is noted that in some embodiments, the sensor 22 remains off until the motor or a spray sequence is initiated, whereupon the sensor 22 is turned on, or otherwise operatively engaged for transmitting electrical signals based on detected waves 34. For instance, a microcontroller can be programmed with the spray sequence and trigger the sensor 22 to detect the acoustic waves 34 only during the spray sequences to prohibit unwanted detection of sounds from registering, e.g., background noise. Further, it is noted that the sound profile detected by the sensor 22 for the methods disclosed herein can be emanated from and detected from any portion of the dispensing system 10, such as, and not limited to, the external discharge orifice 32, the conduit 14, the internal discharge orifice 30, the container 28, and the like, taken alone or in any combination. Any or all of these are contemplated to provide sound that can be detected at the sensor 22 and can be taken in combination with other embodiments disclosed herein, such as unique sounds created with product formulations, mechanical structures in the flow pathway, and the like.

Upon detection of the acoustic waves 34, the sensor 22 generates electrical voltage signals that may be preamplified at 60. The preamplified signals are filtered at 62 with various high pass filters, or other filters as known in the art, which may omit unnecessary background noise, e.g., activity in the room, a dog barking, a television, a kitchen noise, and the like. Filtering may also separate frequency characteristics for further processing, for instance, analyzing sound pressure levels only for frequencies within certain ranges, filtering out background noises to distinguish sounds that are cues for initiating an operational sequence, such as clapping, and the like. Notably, one skilled in the art would realize other common filtering schemes may be preferably applied to obtain filtered signals, and such preferences may be dependent on available circuitry, computational power and the like. The filtered signal can be analyzed for an RMS sound pressure level at 64, which is evaluated at logic 66 to determine whether the container 28 is full, empty, partially full, near empty, etc. In some aspects, a full or empty state is determined by measuring a "difference" in the sound pressure level readings between a full and empty container. In another aspect, the full or empty state is determined based on the RMS sound pressure level falling below the threshold level, which may indicate that the container 28 is low or empty as described in preceding paragraphs. For instance, a preprogrammed threshold level may be queried upon during each spray, or a measured spray from a full container 28 is recorded as a threshold level and any pre-specified variations that are realized in subsequent sprays are indicative of low or empty containers 28.

Upon detection of an empty or near empty container 28, the dispensing system 10 can notify the user of the status and/or modify an operating parameter of the dispensing system 10. For example, notifying the user may comprise emitting a tone, illuminating an indication light, automatically placing a refill or reorder purchase through an internet connection, sending an email or other message to the user with a status alert, etc. The dispensing system 10 may be configured to enter a different mode of operation, including reducing power or battery consumption by stopping spraying, changing the time intervals between sprays, activating alternate dispensing systems and/or sources, etc. In a different embodiment, a Fourier Transform or Fast Fourier Transform may be applied at 68 to further filter specific frequencies for input to the classifying mechanism.

Exemplary Embodiment of a Dispensing System

Figure 7:
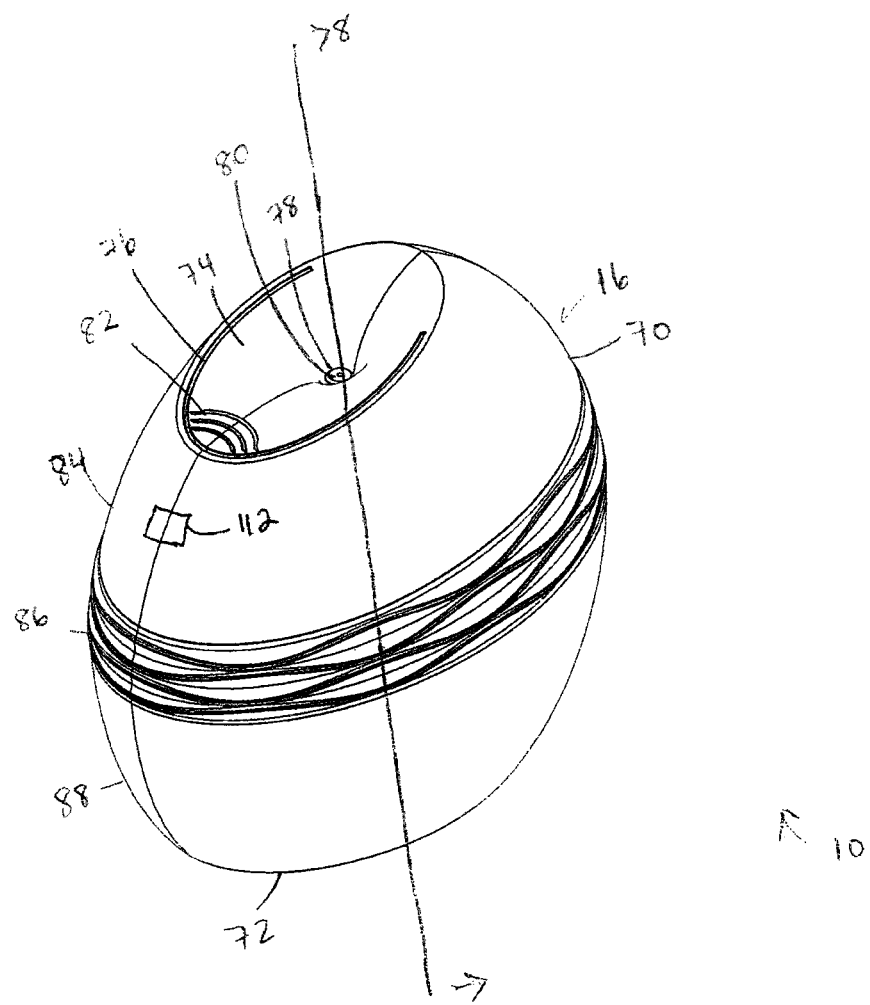
FIG. 7 is an isometric view of an exemplary embodiment of a dispensing system.
Figure 8A:
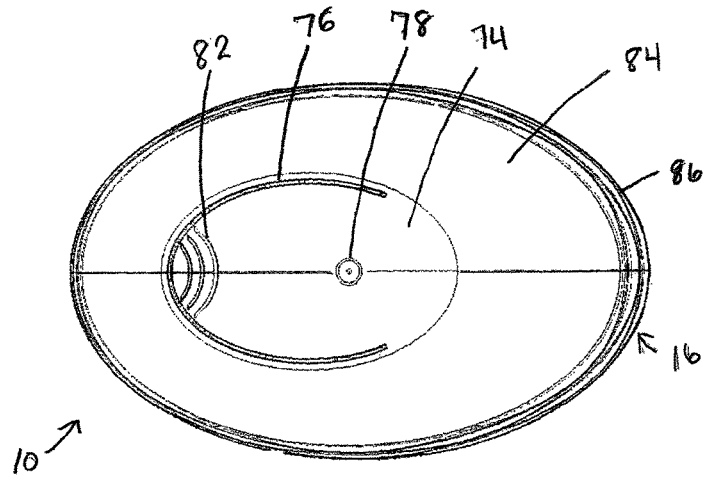
FIG. 8A is a top elevational view of the dispensing system of FIG. 7.
Figure 8B:
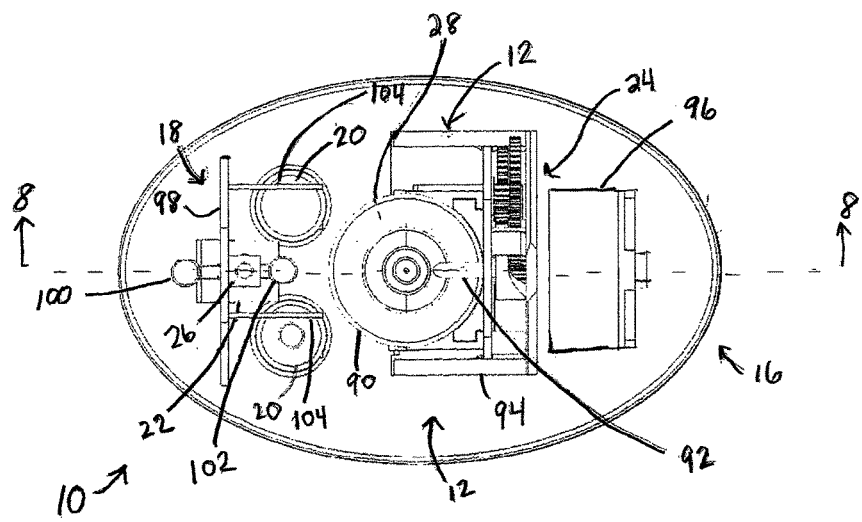
FIG. 8B is a top elevational view similar to FIG. 8A with portions removed.
Figure 9:
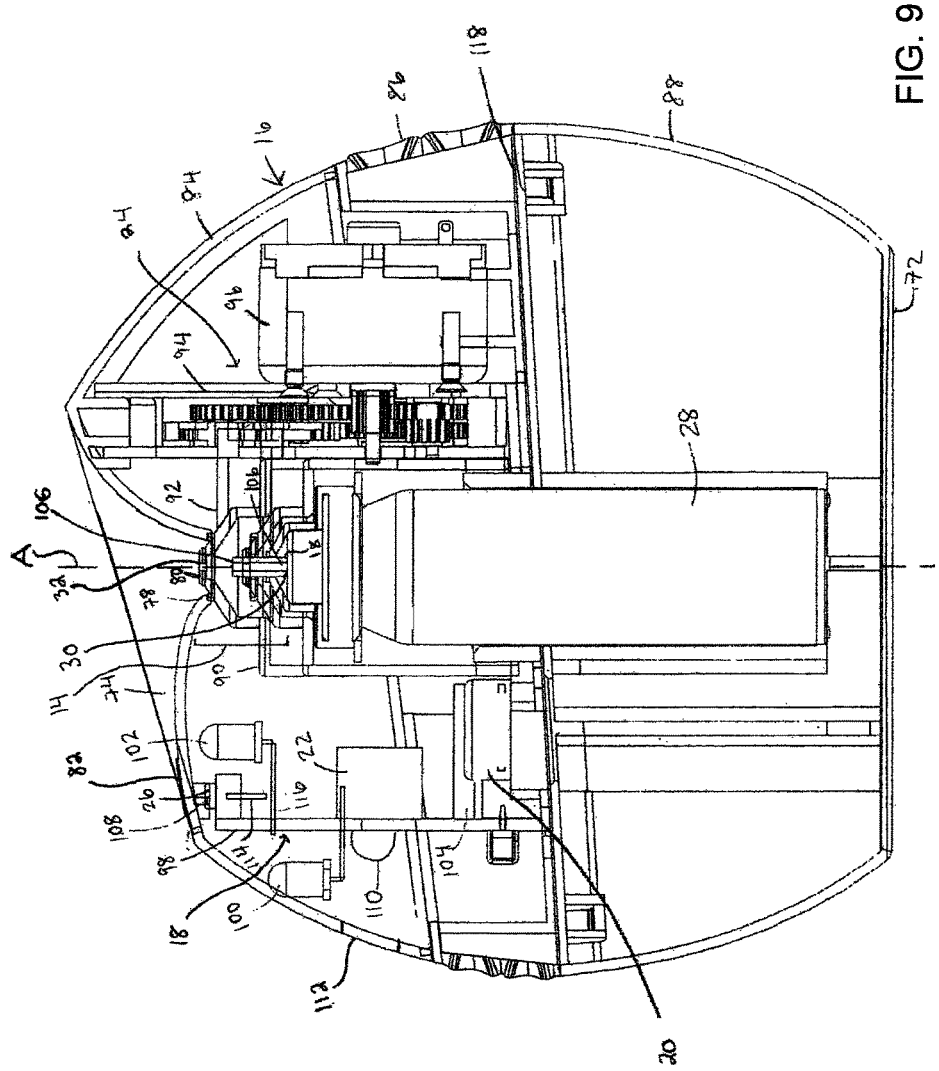
FIG. 9 is a cross sectional view taken along lines 8-8 of FIGS. 7 and 8B.
Figure 10A:
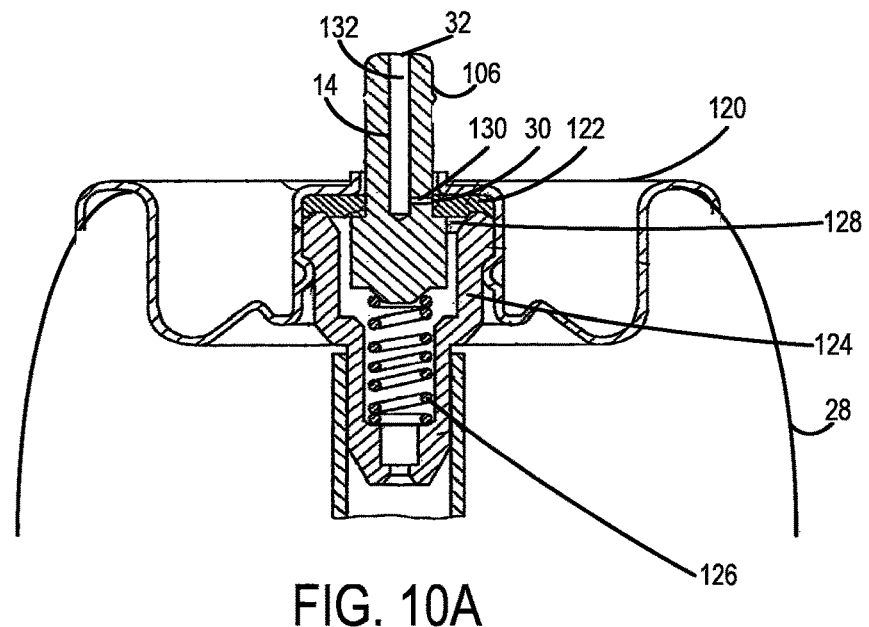
FIG. 10A is a partial cross-sectional view of an aerosol container with a spray valve assembly and a conduit.
Figure 10B:
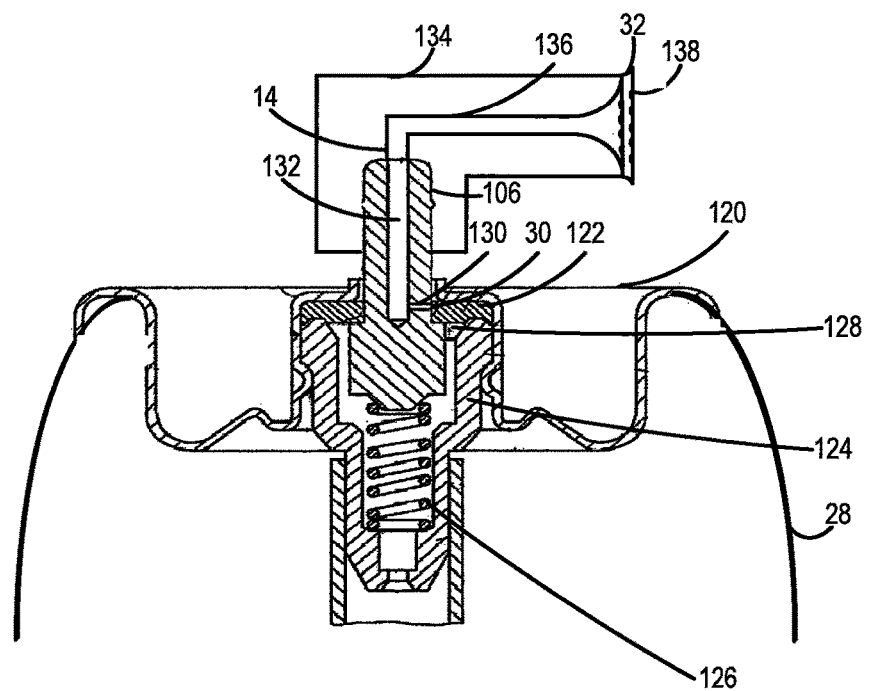
FIG. 10B is a partial cross-sectional view of FIG. 10A with a sprayer head added to the conduit.
Figure 11:
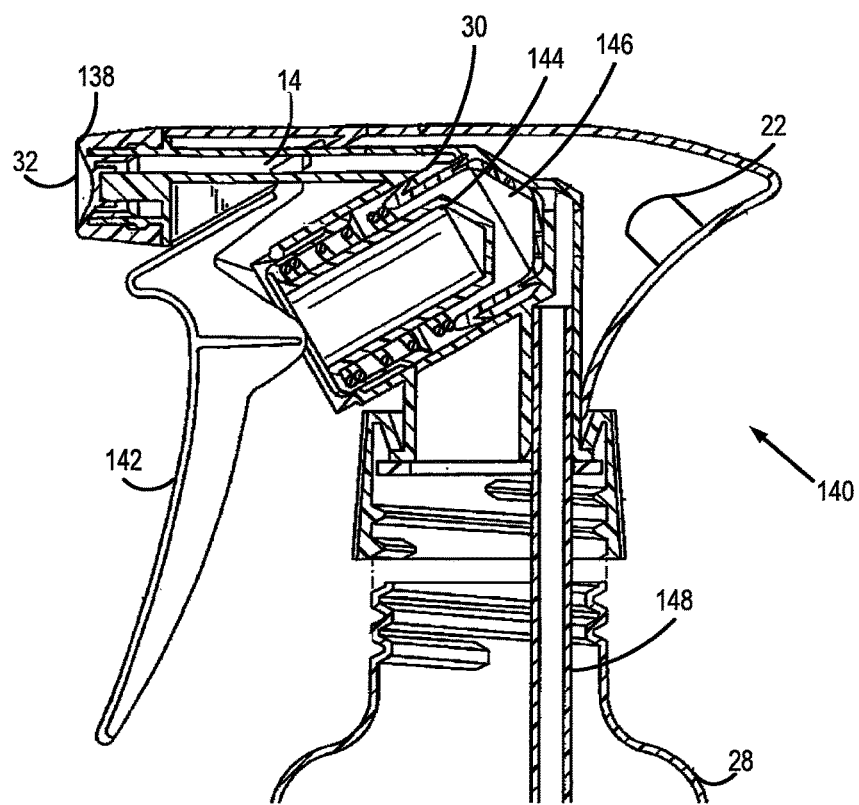
FIG. 11 is a partial cross-sectional view of a pump-type spray container with a valve assembly and a conduit.
Figure 12:
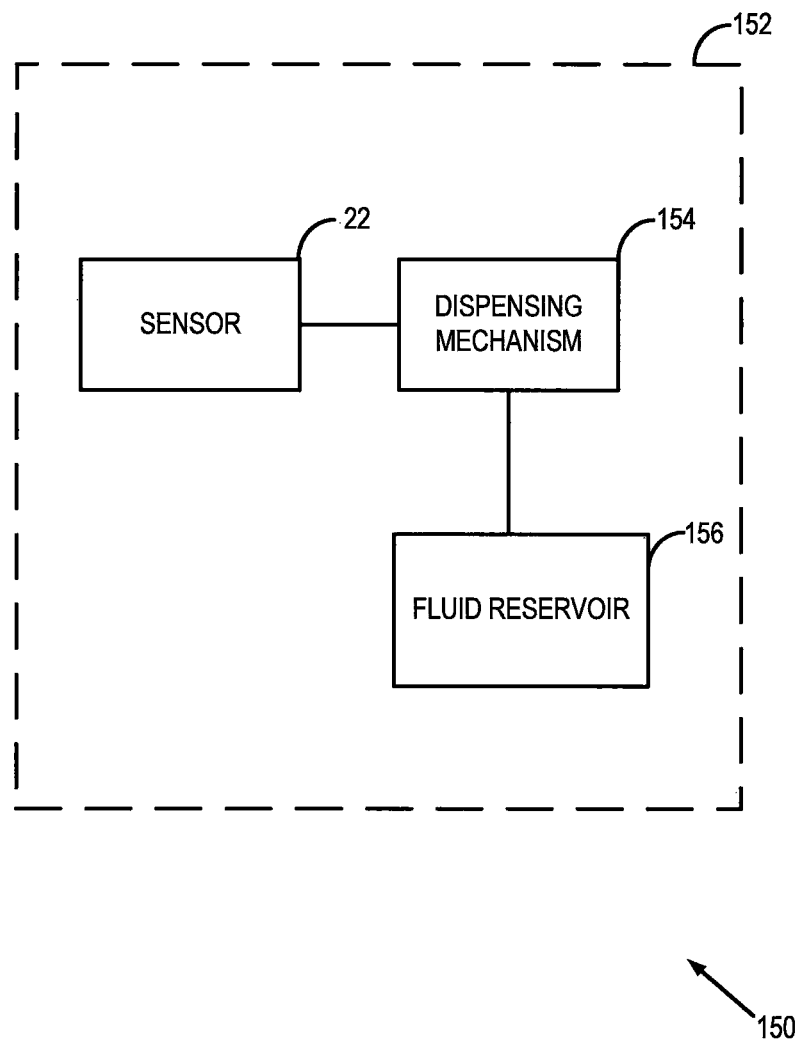
FIG. 12 is a schematic representation of various alternative dispensing systems.

FIGS. 7-9 illustrate one example of a dispensing system, which includes a dispenser enclosed within a housing. The dispenser is adapted for dispensing the contents of an aerosol container, which may include any fluid, volatile material, or product known to those of skill in the art. The dispenser may be one of the devices described in Carpenter et al. U.S. patent application Ser. No. 11/725,402, Furner et al. U.S. patent application Ser. No. 13/302,911, Gasper et al. U.S. patent application Ser. No. 13/607,581, and Baranowski et al. U.S. patent application Ser. No. 13/607,581. The dispenser generally includes an actuation mechanism, controller, input device, power source, and sensor, see, e.g., FIG. 1.

Referring to FIG. 7, the dispensing system 10 comprises a housing 16 having arcuately-shaped sidewalls 70 that extend from a perimeter of a generally oval-shaped flat base 72 toward a perimeter of a generally oval-shaped hinged roof 74. The hinged roof 74 is linearly sloped with respect to the flat base 64 and comprises a generally semi-oval cut-out 76 about a portion of its perimeter. The hinged roof 74 provides a funnel-like surface that tapers down toward an orifice 78, which may be centered or otherwise within the surface of the roof 74. The orifice 78 exposes an aligned spray nozzle 80 that is in operative communication with an aerosol container 28 provided within the housing 16. As such, the orifice 78 allows for fluid emission from the dispensing system 10 to a surrounding atmosphere. The hinged roof 74 further provides manual activation guides 82, which may be arcuately-shaped cut-outs, raised or indented ridges, inked markings, or any other indications for receiving a depressive force, e.g., a downward push from a user's finger(s). Upon placement of a depressive force on the activation guides 82, the hinged roof 74 rotates into the housing 16 to make contact with a portion of the dispenser 12 that activates a spray sequence.

In one embodiment, the housing 16 comprises three separable segments, which include a top portion 84, a middle rim 86, and a bottom portion 88. The middle rim 86 may be distinguished from the top and bottom portions 84, 88 by a band having a wave-like or other geometric pattern that is engraved, painted, molded, or otherwise disposed thereon. The portions 84, 88 and rim 76 may be held together by friction fitting, snap fitting, deformation, thread engagement, latching, adhesive, or any other attachment mechanism known to one of skill in the art. In a different embodiment, the housing 16 may be constructed as a single piece by molding or permanently binding various components of the housing 16 together.

FIGS. 8A and 8B illustrate top views of the dispensing system 10. In reference to FIG. 8A, it may be seen that the hinged roof 74 having the cut-out 76 is provided within the top portion 84. The hinged roof 74 is attached to a top portion of the arcuately-shaped sidewalls 70. The sidewalls 70 slope outwardly away from the orifice 78 until reaching an inflection point, which in the present embodiment is at the middle rim 86, whereupon the sidewalls 70 reverse slope and curve inwardly toward the flat base 72 on the bottom portion 88 (see FIG. 7). In other embodiments, the inflection point may be provided on other areas of the middle rim 86, or on the top or bottom portions 84, 88.

In FIG. 8B, the dispensing system 10 is shown with the top portion 84 and the middle rim 86 removed from the bottom portion 88. A power source 20 is shown, which comprises two AA batteries. An aerosol container 28 is also provided with a top portion covered by an aerosol cap 90 that is attached to the actuation mechanism 24. Specifically, the aerosol container 28 provides a reservoir of pressurized fluid or product. The actuation mechanism 24 includes an actuator arm 92 connected to the aerosol cap 90, which is fixed to a portion of a drive train assembly 94 that is in operative communication with a motor 96. The separable housing 16 further provides access to the controller 18, which may comprise a printed circuit board 98 dressed with a first and second LED light 100, 102, a sensor 22, an input device 26, and a pair of power source leads 104. In practice, providing the user with easy access to the various internal components of the housing 16 allows for battery or power source 20 replacement, aerosol container 28 refills, troubleshooting of the controller 18, and the like, which improves overall serviceability of the dispensing system 10.

Turning now to FIG. 9, the aerosol container 28 is shown in fluid communication with a valve stem 106, which are received within the housing 16. In the particular embodiment shown, the valve stem 106 provides a conduit 14 having a fluidly connected internal discharge orifice 30 and an external discharge orifice 32. It can be seen that the aerosol cap 90 encases an upper portion of the container 28 and valve stem 106, such that the spray nozzle 80 provided on the aerosol cap 90 is aligned with the valve stem 106. The aerosol cap 90 is operatively coupled to the motor 96 by means of the drive assembly 94 and the actuator arm 92, such that the motor 96 rotates the gears of the drive assembly 94 to move the actuator arm 92 and its connected aerosol cap 90 upwardly or downwardly about a longitudinal axis A of the container 28 into pre-actuation and actuation positions, respectively. The motor 96 is activated by control from the electrical signals output from the printed circuit board 98 based on the occurrence of various conditions as described above. In one embodiment, the user manually presses down on the manual activation guides 82, which causes a protruding wedge 108 of the hinged roof 74 to contact the input device 26 on the circuit board 98. The input device 26 may be a tactile receiver that causes the circuit board 98 to electronically signal and operate the motor 96.

Still referring to FIG. 9, the actuator arm 92 of the actuation mechanism 24 is a rigid member that is coupled to the motor 96 by the drive train assembly 94. In one embodiment, the actuator arm 92 and the aerosol cap 90 are constructed from a single mold of material. In a pre-actuation position as shown in FIG. 9, the aerosol cap 90 and the spray nozzle 80 provided thereon are positioned slightly above or in non-operative contact with the valve stem 106 of the aerosol container 28. Upon activation, the controller 18 triggers the motor 96 to pull the actuator arm 92 downwardly toward the flat base 72 of the bottom portion 88. The downward movement of the actuator arm 92 impinges the spray nozzle 80 against the valve stem 106 of the container 28, whereupon the valve stem 106 is depressed and exposes a flow pathway. Product is released from the container 28 and the valve stem 106, upwardly through the spray nozzle 80 of the aerosol cap 90 and actuator arm 92, and into the atmosphere through the orifice 78 of the hinged roof 74. Upon completion of the spray sequence, the motor 96 is triggered to move the actuator arm 92 upwardly in return to the pre-actuation position, whereby the valve stem 106 also returns to a sealed pre-actuation position.

In another embodiment, the circuit board 98 is programmed to automatically activate the motor 96 in response to a lapsed time interval, a time of day, sensed external stimuli such as a change in light intensity or sound, and the like. For instance, light sensing elements such as a photodetector or a photodiode light detector, a photoresistor, a photodiode, a solar module, or more specifically, a phototransistor 110, may incorporate an aperture or lens cover 112 within the housing (see FIGS. 7 and 9). The aperture or lens 112 may be configured to ensure a wide field of view for the phototransistor 110 to detect any changes in the intensity of ambient light while also providing protection. Alternatively, or in conjunction with a different sensor 22 and/or a timer, a sound can be detected by a sound sensor to effect activation of the motor, such as a dog barking, footsteps through a room, and so forth.

With reference still to FIG. 9, the circuit board 98 is designed to work off of the power source 20 comprising a battery in contact with the power source leads 104. The circuit board 98 feeds the power to various components including the first and second LED lights 100, 102, the input device 26, the sensor 22, and the motor 96. For instance, the input device 26 comprises a tactile receiver having a conductive pin 114 that upon manual activation makes contact with a conductive LED bridge 116 and forms a complete electrical circuit. The completed circuit allows electricity to flow from the power source 20 to the second LED light 102, which illuminates in turn. In another example, the power source 20 provides power to the sensor 22 only during activation of a spray in order to detect waves emitted from the conduit 14, which in the present embodiment includes the valve stem 106 and portions of the aerosol cap 90 leading to the spray nozzle 80. The sensor 22 outputs an electrical signal based on the detected waves that are subsequently preamplified and processed by components on the circuit board 98 to determine a full or other status of the container 28. Various user alerting mechanisms may be implemented based on results of the signal processing and analysis, e.g., one or both LED lights 100, 102 may illuminate if the aerosol container 28 is near exhaustion, a beep or other sound may be produced by the microphone sensor 22 if an improper aerosol container 28 is inserted, and the like.

In a different embodiment, the sensor 22 further receives power from the power source 20 to detect background waves emitted during the preactuation stage, e.g., to detect particular waves or wave patterns that indicate activity in a room in which the dispensing system 10 is placed. Upon the occurrence of a particular sensor 22 reading, such as a particular sound pressure level or frequency characteristic, a spray sequence may be initiated or blocked. In yet another embodiment, the conduit 14 may be mechanically designed to generate specific frequency profiles during activation, e.g., an audible whistle or a noise at sub or ultra-hearing frequencies. The sensor 22 may be configured to distinguish between different conduits 14, which may indicate whether a preferred or a less preferred container 28 is engaged. For instance, the sensor 22 may determine that the detected frequency profile of the sound created at the conduit 14 is inappropriate and alert the user with an audible or visual indication, and/or terminate future spray sequences until a preferred container 28 is engaged. In this manner, the sensor 22 contributes to the classifying aspect of the dispensing system 10, as described above.

It is further contemplated that the housing 16 provides waveguide properties for the waves emitted from the conduit 14 during activation. For example, the top portion 84 generally provides a dome-shaped chamber in which waves emitted from the centrally-located container 28 may be bounced off of the curved chamber walls and back toward the sensor 22. Further, the middle rim 86 may provide a middle platform 118 extending radially across the housing 16. The middle platform 118 may comprise slots and beams for securing the various components of the dispenser 12 and container 28 described herein, and further may reflect downward traveling waves upwardly toward the sensor 22. The enclosure of the housing 16 effectively reflects some of the sound generated within the housing 16 toward the sensor 22, which aids in the detection abilities of the sensor 22 and allows greater freedom in positioning the sensor 22. For instance, as shown in FIG. 9, the sensor 22 is mounted directly onto the circuit board 98 at a substantial distance from the conduit 14, e.g., the valve stem 106, which is encased within the aerosol cap 90. In other embodiments, the sensor 22 may be mounted proximal the valve stem 106, below the valve stem 106, above the valve stem 106, and any other position within the housing 16 to benefit from the waveguide effects.

Turning now to FIG. 10A, one embodiment of the valving assembly is shown as received on a mounting cup 120 configured to be crimped onto an upper portion of the aerosol container 28. The valving assembly includes the valve stem 106, a valve body 124, and a valve spring 126. The valve stem 106 provides the conduit 14 that is defined between the internal discharge orifice 30 and the external discharge orifice 32. The assembly is in a pre-actuation state in which a gasket 122 provides a seal between the valve body 124 and the valve stem 106. The seal prevents pressurized fluid of an attached container 28 from being released into the internal discharge orifice 30. When the valve assembly is opened during actuation, a pressure differential between the container 28 interior and the atmosphere forces the pressurized fluid out through the external discharge orifice 32 of the valve stem 106. Specifically, the valve stem 106 is depressed downward onto the valve spring 126 such that the internal discharge orifice 30 aligns with a radial opening 128 of the valve body 124, which is in fluid communication with the interior of the container 28. The pressurized fluid flows through the radial opening 128 and internal discharge orifice 30 to reach the conduit 14. The conduit 14 may be arranged as a radial slit 130 in fluid communication with a longitudinal channel 132 that is further in fluid communication with the external discharge orifice 32. The pressurized fluid continues through the conduit 14 and external discharge orifice 32 for release into the atmosphere, whereupon the valve stem 106 is thereafter forced upward by internal forces of the container 28 to re-establish the sealing relationship with the gasket 122. It is contemplated that the valve stem 14 can be modified to cause more turbulent flow during the spray (see FIGS. 4A-D) such that certain sound signatures can be detected by the sensor 22 (not shown).

FIG. 10B shows the embodiment of FIG. 10A with a sprayer head 134 in fluid communication with the longitudinal channel 132 of the valve stem 106. The sprayer head 134 provides a discharge tube 136 that opens to a nozzle 138 for nebulizing the fluid flow. It is contemplated that the external discharge orifice 32 is the nozzle 138 such that the flow pathway provided by the conduit 14 for the pressurized fluid is extended beyond the previous illustration of FIG. 10A. Similarly, any portion of the longitudinal channel 132, discharge tube 136, and nozzle 138 may be mechanically modified to produce certain sound signatures for detection by the sensor 22 (not shown).

Turning now to FIG. 11, a pump-type sprayer head 140 having a sensor 22 mounted therein is shown in a pre-actuation state. The pump-type sprayer 140 provides the conduit 14 between the internal discharge orifice 30 and external discharge orifice 32, which is provided adjacent a nozzle 138. As a trigger 142 is drawn inwardly during an actuation state, a piston 144 creates pressure to force a volume of fluid stored in a chamber 146 through the internal discharge orifice 30, the conduit 14, and the external discharge orifice 32 for a directional spray through the nozzle 138. As the trigger returns to the pre-actuation state, a pressure differential created by the piston 144 vacuums fluid upwardly through a tube 148 from the pump-type spray container 28. The fluid refills the chamber 146 in preparation for a subsequent actuation. The sensor 22 may be configured to detect a variety sounds, including sound generated at the conduit 14 as described above, sounds from the nozzle 138 upon exit of the fluid, and further, sounds in a post-actuation state when fluid, or lack thereof, is drawn upwardly through the tube 148. For instance, upon a failure to detect sound, or a sufficient threshold of sound, during the post-actuation stage that corresponds to no or diminished fluid flowing through the tube 148, the sensor 22 can indicate that the fluid level in the container 28 is depleted or low.

Referring to FIG. 12, a general schematic representation of other dispensing systems is shown. The dispensing device 150 generally comprises a housing 152 containing a dispensing mechanism 154 in operative communication with a fluid reservoir 156 and a sensor 22. It is contemplated that the dispensing device 150 may be utilized for any product stored in the fluid reservoir 156, which may be non-pressurized in the present embodiment. As non-limiting examples, such reservoirs may contain conventional oils, air fresheners, fabric fresheners, refreshers, deodorizers, sanitizers, disinfectants, soaps, insecticides, insect repellants, fertilizers, herbicides, fungicides, algaecides, pesticides, rodenticides, paints, deodorants, body sprays, hair sprays, topical sprays, cleaners, polishes, and shoe or footware spray products. In line with the embodiments described above, the sensor 22 may be configured to detect any sound that is emitted during an actuation stage of the dispensing device 150, and specifically during the actuation phase provided by the dispensing mechanism 154. It is contemplated that in addition to the various types of actuation mechanisms 24 described above, the dispensing mechanism 154 may include solenoid actuators, bi-metallic actuators, piezo-electric actuators, heating a reservoir 156, heating a wick extending from or into a reservoir 156, running a fan adjacent an aperture of a reservoir or a wick extending from a reservoir 156, running a fan within a housing 152 to assist in dispersal of a product, activating a piezo-electric plate adjacent a wick to volatize a fluid thereon, opening a window or otherwise removing an obstruction from an aperture to assist in the dispersal or diffusion of product from the dispensing device 150, or any other means for diffusing. Still further, the dispensing device 150 may include a plurality of dispensing mechanisms 154 to dispense product from a plurality of fluid reservoirs 156, whether they are pressurized or non-pressurized. Similarly, a plurality of sensors 22 may be provided.

The dispensing mechanism 156 and/or sensor 22 may further comprise or be in operative association with a power source, a sensor, an input device, and/or a controller, any of which may or may not be disposed within the housing 152. In one embodiment, the dispensing mechanism 154 is a solenoid actuator that typically consists of an electrically operated coil that produces magnetic fields to move an armature up or down and thereby effect collapse or rebound of a spring. The spring is typically in connection with a stem of a valve on the reservoir 156. The solenoid actuator is contemplated to produce different sound levels or frequencies of sound depending on the amount of product being emitted from the reservoir 156 and/or depending on the level of product remaining in the reservoir 156. For instance, the solenoid actuator may produce a lower sound level and/or frequency if little force is applied during actuation due to a low, or empty reservoir 156 or low dose of product to be released. On the other hand, for a full reservoir 156 or a full dose of product to be released, the solenoid actuator may produce a greater sound level and/or generate other frequencies. In one embodiment, the solenoid actuator is physically modified or adapted to create certain sound profiles that can be detected by the sensor 22 for further implications in modes of operation, such as changes in time sequences, threshold levels, and various operational parameters or modes as described previously. In one particular embodiment, a threshold level of the solenoid actuator may comprise a property of sound that is predetermined to correspond to a certain status of the reservoir 156, such as a low or empty status.

Indeed, it is contemplated that any of the above disclosure could be used in connection with sensing the sound of a fluid emitted from numerous types of dispensing mechanisms described herein. For example, in one embodiment, fluid emitted through a piezo electric plate disposed adjacent to a wick may be used to detect an end of life based on the sound that is generated as the fluid, or lack thereof, passes through the plate. In another embodiment, a fan in communication with a wick that receives fluid from a reservoir 156 may produce certain aero-acoustical blade noises based on the product and amount thereof being released to indicate an empty or low fluid reservoir. In yet another embodiment, any dispensing mechanism 156, such as a piezo electric motor, bi-metallic motor, nitinol or muscle wire actuator, in connection with the dispensing of the fluid itself, may provide various discernible sounds that indicate a status of the reservoir 156.

All documents cited in the Detailed Description of the Invention are, in relevant part, incorporated herein by reference; the citation of any document is not to be construed as an admission that it is prior art with respect to the present invention.

INDUSTRIAL APPLICABILITY

Numerous modifications will be apparent to those skilled in the art in view of the foregoing description. Accordingly, this description is to be construed as illustrative only and is presented for the purpose of enabling those skilled in the art to make and use what is herein disclosed and to teach the best mode of carrying out same. The exclusive rights to all modifications which come within the scope of this disclosure are reserved.

I claim:
1. A dispensing system, comprising:
   a conduit including a valve stem of an aerosol container and a volumetric capacity between an internal discharge orifice for receipt of a flow of pressurized fluid from the valve stem and an external discharge orifice;
   a volume of pressurized fluid; and
   a sensor,
   wherein the fluid has a volumetric flow rate of about 0.05 ml/ms to about 15 ml/ms when released into the volumetric capacity from the internal discharge orifice,
   wherein the sensor detects a sound at the external discharge orifice,
   wherein the sensor detects a level of the sound that corresponds to different flow rates, and
   wherein a ratio of a threshold level of sound to the detected level of sound during an actuation state is less than one at a first stage and substantially unity at a second stage.
2. The dispensing system of claim 1, wherein the first stage corresponds to a positive level of product in a container and the second stage corresponds to an empty or low amount of product in the container.
3. The dispensing system of claim 2, wherein a user perceivable cue is provided to indicate the second stage.
4. A dispensing system comprising:
   a conduit including a valve stem of an aerosol container and a volumetric capacity between an internal discharge orifice for receipt of a flow of pressurized fluid from the valve stem and an external discharge orifice;
   a volume of pressurized fluid; and
   a sensor,
   wherein the fluid has a volumetric flow rate of about 0.05 ml/ms to about 15 ml/ms when released into the volumetric capacity from the internal discharge orifice,
   wherein the sensor detects a sound at the external discharge orifice,
   wherein the sensor detects a frequency characteristic of the sound that is generated by at least one of a shape of the conduit and a product formulation, and
   wherein a controller initiates or prohibits at least one of an initial or subsequent actuation of the dispensing system based on the detected frequency characteristic.
5. The dispensing system of claim 4, wherein the controller implements an operational parameter associated with the detected frequency characteristic during actuation of the dispensing system.

6. The dispensing system of claim 5, wherein the controller implements an operation associated with the detected frequency characteristic.

7. A dispensing system, comprising:
a conduit including a valve stem of an aerosol container and a volumetric capacity between an internal discharge orifice for receipt of a flow of pressurized fluid from the valve stem and an external discharge orifice;
a volume of pressurized fluid; and
a sensor,
wherein the fluid has a volumetric flow rate of about 0.05 ml/ms to about 15 ml/ms when released into the volumetric capacity from the internal discharge orifice,
wherein the sensor detects a sound at the external discharge orifice, and
wherein a ratio of the level of volumetric flow rate during an actuation state to a threshold level of volumetric flow rate is less than one at a first status and substantially unity at a second status.

8. A dispensing system, comprising:
a sensor for detecting a sound emitted from a reservoir of fluid having a conduit; and a controller having a plurality of preprogrammed operational parameters associated with a plurality of preprogrammed frequency characteristics, wherein the controller compares a frequency characteristic of the sound to the plurality of preprogrammed frequency characteristics, and wherein the sensor further detects a sound from an environment to activate the dispensing system.

9. The dispensing system of claim 8, wherein the controller determines a match between the detected frequency characteristic and at least one of the plurality of preprogrammed frequency characteristics.

10. The dispensing system of claim 9, wherein the controller implements the preprogrammed operation parameter associated with the matched preprogrammed frequency characteristic.

* * * * *